US008703999B2

(12) United States Patent
Barnicki et al.

(10) Patent No.: US 8,703,999 B2
(45) Date of Patent: Apr. 22, 2014

(54) HYDROCARBOXYLATION OF METHYLENE DIPROPIONATE IN THE PRESENCE OF PROPIONIC ACID AND A HETEROGENEOUS CATALYST

(75) Inventors: Scott Donald Barnicki, Kingsport, TN (US); Robert Thomas Hembre, Johnson City, TN (US); Stephen Neal Falling, Kingsport, TN (US); Mesfin Ejerssa Janka, Kingsport, TN (US); Kelley Margaret Moran, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 24 days.

(21) Appl. No.: 13/431,386

(22) Filed: Mar. 27, 2012

(65) Prior Publication Data

US 2013/0261337 A1    Oct. 3, 2013

(51) Int. Cl.
*C07C 51/42* (2006.01)

(52) U.S. Cl.
USPC ............ 562/580; 562/524; 562/525; 562/606

(58) Field of Classification Search
USPC .......................................... 562/524, 525, 580
See application file for complete search history.

(56) References Cited

U.S. PATENT DOCUMENTS

| 2,152,852 A | 4/1939 | Loder |
| 2,153,064 A | 4/1939 | Larson |
| 2,211,624 A | 8/1940 | Loder et al. |
| 2,211,625 A | 8/1940 | Loder |
| 2,298,138 A | 10/1942 | Loder |
| 2,436,209 A | 2/1948 | Elgin |
| 2,443,482 A | 6/1948 | Shattuck |
| 3,333,924 A | 8/1967 | Hazen et al. |
| 3,751,453 A | 8/1973 | Kurkov et al. |
| 3,754,028 A | 8/1973 | Lapporte et al. |
| 3,801,627 A | 4/1974 | Kurkov et al. |
| 3,859,349 A | 1/1975 | Cody |
| 3,911,003 A | 10/1975 | Suzuki |
| 3,927,078 A | 12/1975 | Lapporte et al. |
| 3,948,977 A | 4/1976 | Suzuki |
| 3,948,986 A | 4/1976 | Suzuki |
| 4,016,208 A | 4/1977 | Suzuki |
| 4,052,452 A | 10/1977 | Scardigno et al. |
| 4,087,470 A | 5/1978 | Suzuki |
| 4,112,245 A | 9/1978 | Zehner et al. |
| 4,128,575 A | 12/1978 | Leupold et al. |
| 4,136,112 A | 1/1979 | Bakshi |
| 4,140,866 A | 2/1979 | Nielsen |
| 4,153,809 A | 5/1979 | Suzuki |
| 4,228,305 A | 10/1980 | Suzuki |
| 4,275,234 A | 6/1981 | Baniel et al. |
| 4,291,007 A | 9/1981 | Baniel |
| 4,308,397 A | 12/1981 | Suzuki |
| 4,366,333 A | 12/1982 | Wilkes |
| 4,409,395 A | 10/1983 | Miyazaki et al. |
| 4,431,486 A | 2/1984 | Balmat |
| 4,440,734 A | 4/1984 | Kougioumoutzakis |
| 4,501,917 A | 2/1985 | Schmidt et al. |
| 4,691,048 A | 9/1987 | Hughes et al. |
| 4,824,997 A | 4/1989 | Macfarlane et al. |
| 4,935,102 A | 6/1990 | Berg |
| 4,966,658 A | 10/1990 | Berg |
| 4,990,629 A | 2/1991 | Souma |
| 5,026,927 A | 6/1991 | Andrews et al. |
| 5,210,335 A | 5/1993 | Schuster et al. |
| 5,214,219 A | 5/1993 | Casale et al. |
| 5,276,181 A | 1/1994 | Casale et al. |
| 5,423,955 A | 6/1995 | Berg |
| 5,455,372 A | 10/1995 | Hirai et al. |
| 5,723,662 A | 3/1998 | Ebmeyer et al. |
| 5,932,772 A | 8/1999 | Argyropoulos et al. |
| 5,952,530 A | 9/1999 | Argyropoulos et al. |
| 6,252,121 B1 | 6/2001 | Argyropoulos et al. |
| 6,291,725 B1 | 9/2001 | Chopade et al. |
| 6,294,700 B1 | 9/2001 | Kanel et al. |
| 6,303,829 B1 | 10/2001 | Kanel et al. |
| 6,307,108 B1 | 10/2001 | Argyropoulos et al. |
| 6,307,109 B1 | 10/2001 | Kanel et al. |
| 6,307,110 B1 | 10/2001 | Argyropoulos et al. |
| 6,310,260 B1 | 10/2001 | Argyropoulos et al. |
| 6,376,723 B2 | 4/2002 | Drent et al. |
| 7,122,698 B2 | 10/2006 | Yoshida et al. |
| 7,164,040 B2 | 1/2007 | Kuroda et al. |
| 7,223,885 B2 | 5/2007 | Van Krieken |

(Continued)

FOREIGN PATENT DOCUMENTS

| DE | 3133353 C2 | 3/1983 |
| EP | 0 114 657 B1 | 3/1987 |

(Continued)

OTHER PUBLICATIONS

Notification of Transmittal of the International Search Report and the Written Opinion of the International Search Authority with Mail Date of Mar. 15, 2012 for International Application No. PCT/US2011/051490.

Notification of Transmittal of the International Search Report and the Written Opinion of the International Search Authority with Mail Date of Nov. 28, 2011 for International Application No. PCT/US2011/047842.

Celik et al., "Synthesis of precursors to ethylene glycol from formaldehyde and methyl formate catalyzed by heteropoly acids", Journal of Molecular Catalysis A: Chemical 288, (2008), pp. 87-96.

Celik et al., "Vapor-phase carbonylation of dimethoxymethane of H-Faujasite", Angewandte. Chemie Int. Ed. 2009, 48, pp. 4813-4815.

(Continued)

*Primary Examiner* — Brian J Davis
(74) *Attorney, Agent, or Firm* — Jennifer Knight

(57) ABSTRACT

Disclosed is a process for the production and purification of glycolic acid or glycolic acid derivatives by the carbonylation of methylene dipropionate in the presence of a solid acid catalyst and propionic acid. This invention discloses hydrocarboxylations and corresponding glycolic acid separations wherein the propionic acid stream is readily removed from the glycolic acid and the propionic acid is recycled.

20 Claims, 1 Drawing Sheet

(56) References Cited

U.S. PATENT DOCUMENTS

| | | | |
|---|---|---|---|
| 7,439,391 | B2 | 10/2008 | Gallagher et al. |
| 7,615,671 | B2 | 11/2009 | Puckette et al. |
| 7,709,689 | B2 | 5/2010 | Kilner et al. |
| 7,772,423 | B2 | 8/2010 | Celik et al. |
| 8,466,328 | B2 | 6/2013 | Barnicki et al. |
| 2004/0222153 | A1 | 11/2004 | Baniel et al. |
| 2006/0160197 | A1 | 7/2006 | Li et al. |
| 2007/0123739 | A1 | 5/2007 | Crabtree et al. |
| 2008/0275277 | A1 | 11/2008 | Kalagias |
| 2009/0143612 | A1 | 6/2009 | Puckette et al. |
| 2011/0144388 | A1 | 6/2011 | Sun et al. |
| 2011/0166383 | A1 | 7/2011 | Sun et al. |
| 2012/0046481 | A1 | 2/2012 | Barnicki et al. |
| 2012/0046500 | A1 | 2/2012 | Barnicki et al. |
| 2012/0078010 | A1 | 3/2012 | Barnicki et al. |

FOREIGN PATENT DOCUMENTS

| | | | |
|---|---|---|---|
| EP | 0 676 239 | A2 | 10/1995 |
| EP | 1 679 331 | A1 | 7/2006 |
| GB | 508383 | A | 6/1939 |
| GB | 1499245 | A | 1/1978 |
| GB | 2179337 | A | 7/1986 |
| IL | 89044 | A | 3/1993 |
| JP | 56100741 | A | 8/1981 |
| JP | 56131546 | A | 10/1981 |
| JP | 56133237 | A | 10/1981 |
| JP | 5746934 | A | 3/1982 |
| JP | 57040442 | A | 3/1982 |
| JP | 57102837 | A | 6/1982 |
| JP | 6228045 | A | 8/1994 |
| JP | 1999147042 | A | 6/1999 |
| JP | 2004131411 | A | 4/2004 |
| SU | 1436453 | A1 | 9/1996 |
| WO | WO 97/15543 | A1 | 5/1997 |
| WO | WO 2006/069127 | A1 | 6/2006 |
| WO | WO 2009/140850 | A1 | 11/2009 |
| WO | WO 2012/040007 | A2 | 3/2012 |
| WO | WO 2012/130316 | A1 | 10/2012 |

OTHER PUBLICATIONS

Asci, Yavuz Selim et al. "Extraction of Glycolic Acid from Aqueous Solutions by Amberlite LA-2 in Difference Diluent Solvents" J. Chem Eng. Data 2009, 54, 2791-2794.
Bizek, Vladislav et al. "Amine Extraction of Hydroxycarboxylic Acids. 1. Extraction of Citric Acid with 1-Octanol/n-Heptane Solutions of Trialkylamine" Ind. Eng. Chem. Res. 1992, 31, 1554-1562.
Tamada, Janet A. et al. "Extraction of Carboxylic Acids with Amine Extractants. 1. Equilibria and Law of Mass Action Modeling" Ind. Eng. Chem. Res. 1990, 29, 1319-1326.
Smith, E. Lester "The Acid-Binding Properties of Long-Chain Aliphatic Amines" J.S.C.I., 67, Feb. 1948 pp. 48-51.
Walker, "Formaldehyde", Walker, ACS Monograph, Washington, DC., ACS, 1964, p. 95.
Eyal, A., et al. "Recovery and Concentration of Strong Mineral Acids from Dilute Solutions Through LLX III. A "Temperature Swing" Based Process" Solvent Extraction and Ion Exchange, 9 (2), 223-236 (1991).
Eyal, A.M., et al. "Recovery and Concentration of Strong Mineral Acids from Dilute Soltions Through LLX. I: Review of Parameters for Adjusting Extractant Properties and Analysis of Process Options" Solvent Extraction and Ion Exchange, 9 (2), 195-210 (1991).
Eyal, A.M., et al. "Recovery and Concentration of Strong Mineral Acids from Dilute Solutions Through LLX. II. Reversible Extraction with Branched-Chain Amines" Solvent Extraction and Ion Exchange, 9(2), 211-222 (1991).
Eyal, Aharon, et al. "Extraction of Strong Mineral Acids by Organic Acid-Base Couples", Ind. Eng. Chem. Process Des. Dev., (1982), vol. 21, No. 2, pp. 334-337.
"Handbook of Solvent Extraction'" Krieger Publishing Company, Malabar, FL, 1991, pp. 275-501.

Treybal, Robert E. "Methods of Calculation II. Stagewise Contact, Multicomponent Systems", Liquid Extraction, $2^{nd}$ Edition, McGraw-Hill Book Company, New York. 1963, pp. 275-276.
Treybal, "Liquid Extraction," $2^{nd}$ Ed., McGraw-Hill Book Company, New York, NY, 1963, pp. 349-366.
Gerberich, H. Robert, et al., "Formaldehyde", Kirk-Othmer Encyclopedia of Chemical Technology, vol. 11, $4^{th}$ Edition, 1994, pp. 929-950.
Treybal, Robert E., Liquid Extraction, $2^{nd}$ Ed., McGraw Hill Book Company, 1963, pp. 248-252.
Lynch, Kathleen M., et al., "Improved Preparations of 3-Chloro-2(chloromethyl)-1-propene and 1,1-Dibromo-2,2-bis(chloromethyl)-cyclopropane: Intermediates in the Synthesis of [1.1.1]Propellane", J. Org. Chem, 60, (1995), pp. 4666-4668.
"Tray Design and Operation", Distillation Design, McGraw-Hill, New York (1992), Chapter 6, pp. 259-363.
"Packing Design and Operation", Distillation Design, McGraw-Hill, New York, (1992), Chapter 8, pp. 421-521.
Seader, J.D., Ph.D, et al., "Distillation", Perry's Handbook of Chemical Engineering, Section 13, $7^{th}$ Ed., McGraw-Hill Book Co. 1999.
Lee, Sang Young, et al., "Carbonylation of Formaldehyde over Ion Exchange Resin Catalysts. 1. Batch Reactor Studies", Ind. Eng. Chem. Res., 32, (1993), pp. 253-259.
Xu, Qiang, et al., "Preparation and Catalytic Application of Cationic Metal Carbonyls", Science and Technology in Catalysis, (2002), pp. 215-218.
Xu, Qiang, "Metal carbonyl cations: generation, characterization and catalytic application", Coordination Chemistry Reviews, 231, (2002), pp. 83-108.
Suzuki, S., et al., "Ethylene Glycol from Methanol and Synthesis Gas via Glycolic Acid", Catalytic Conversions of Synthesis Gas and Alcohols to Chemicals, (1984). pp. 221-247.
Wang, Zheng Bao, et al., Carbonylation of Formaldehyde with Carbon Monoxide over Cation-Exchange Resin Catalysts, Bull. Chem. Soc. Jpn., 72, (1999), pp. 1935-1940.
Sano, Tsunejo, et al., "Synthesis of 1,3-dioxolan-4-one from trioxane and carbon monoxide on Hzsm-5 zeolite", Chem. Community, (1997), pp. 1827-1828.
Souma, Yoshie, "Carbonylation at Ambient Pressure in Strong Acids", Journal of Synthetic Organic Chemistry, vol. 41, No. 6, (1983), pp. 561-569.
Soma, Yoshie, et al., "Normal-Pressure CO Addition Reaction of Formaldehyde and Related Compounds on Copper Carbonyl Catalyst", Catalyst 23, (1981), pp. 48-50.
Li, Tao, et al., "Carbonylation of formaldehyde catalyzed by p-toluenesulfonic acid", Catalysis Today, 111, (2006), pp. 288-291.
Souma, Yoshie, et al., "Synthesis of tert.-Alkanoic acid catalyzed by $Cu(CO)^+_n$ and $Ag(CO)^+_2$ under atmospheric pressure", Catalysis Today, 36, (1997), pp. 91-97.
Hendriksen, Dan E., "Intermediates to Ethylene Glycol: Carbonylation of Formaldehyde Catalyzed by NAFION Solid Perfluorosulfonic Acid Resin", Prep. A.C.S. Div. Fuel Chem., 28, (1983), pp. 176-190.
Bhattacharyya, S.K., et al., "High-Pressure Synthesis of Glycolic Acid from Formaldehyde, Carbon Monoxide, and Water in Presence of Nickel, Cobalt, and Iron Catalysts", Advanced Catalysts, 9, (1957), p. 625-635.
Wegescheider, Rud., et al., "Addition of Acid Anhydrides to Aldehydes and Ketones", Royal and Imperial University of Vienna, presented at the meeting of Nov. 4, 1909, pp. 1-47.
King, Walter D., et al. "The Acid-Catalyzed Reaction of Acetic Anhydride with Some Oxocanes", Journal of Applied Polymer Science, vol. 18, (1974) pp. 547-554.
He, Dehua, et al., "Condensation of formaldehyde and methyl formate to methyl glycolate and methyl methoxy acetate using heteropolyacids and their salts", Catalysis Today, 51, (1999), pp. 127-134.
Co-pending U.S. Appl. No. 12/889,045, filed Sep. 23, 2010, Scott Donald Barnicki, et al.
Co-pending U.S. Appl. No. 13,208,399, filed Aug. 12, 2011, Scott Donald Barnicki, et al.
Co-pending U.S. Appl. No. 13/431,335, filed Mar. 27, 2012, Scott Donald Barnicki, et al.

(56) References Cited

OTHER PUBLICATIONS

Co-pending U.S. Appl. No. 13/431,358, filed Mar. 27, 2012, Scott Donald Barnicki, et al.
Co-pending U.S. Appl. No. 13/431,369, filed Mar. 27, 2012, Scott Donald Barnicki, et al.
Co-pending U.S. Appl. No. 13/431,402, filed Mar. 27, 2012, Scott Donald Barnicki, et al.
Co-pending U.S. Appl. No. 13/431,308, filed Mar. 27, 2012, Scott Donald Barnicki, et al.
Co-pending U.S. Appl. No. 13/491,954, filed Jun. 8, 2012 Mesfin Ejerssa Janka.
USPTO Notice of Allowance for U.S. Appl. No. 12/889,045 dated Jul. 18, 2012.
Notification of Transmittal of the International Search Report and the Written Opinion of the International Search Authority with Mail Date of Aug. 13, 2013 for International Application No. PCT/US2013/033458.
Notification of Transmittal of the International Search Report and the Written Opinion of the International Search Authority with Mail Date of Jun. 25, 2013 for International Application No. PCT/US2013/033501.
Notification of Transmittal of the International Search Report and the Written Opinion of the International Search Authority with Mail Date of Aug. 16, 2013 for International Application No. PCT/US2013/033410.
Notification of Transmittal of the International Search Report and the Written Opinion of the International Search Authority with Mail Date of Jun. 21, 2013 for International Application No. PCT/US2013/033520.
Notification of Transmittal of the International Search Report and the Written Opinion of the International Search Authority with Mail Date of Jun. 21, 2013 for International Application No. PCT/US2013/033411.
Notification of Transmittal of the International Search Report and the Written Opinion of the International Search Authority with Mail Date of Jul. 8, 2013 for International Application No. PCT/US2013/033494.
Notification of Transmittal of the International Search Report and the Written Opinion of the International Search Authority with Mail Date of Jul. 12, 2013 for International Application No. PCT/US2013/033446.
Co-pending U.S. Appl. No. 13/896,706, filed May 17, 2013, Scott Donald Barnicki, et al.
USPTO Notice of Allowance for U.S. Appl. No. 12/889,065 dated Oct. 15, 2012.
Hou-Yong, Sun, et al. "Reactive extraction of glycolic acid in high content solution with tri-n-octylamine" Journal of Chemical Engineering of Chinese Universities, Feb. 2007, vol. 21 pp. 26-30.
Baniel, A., et al., "Acid-Base Couple Solvents in Recovery of Mineral Acids From Waste Streams", Proceedings of $2^{nd}$ International Conference on Separations Science and Technology, Oct. 1-4, 1989, pp. 667-674.
Malinowski, J. J. "Evaluation of Liquid Extraction Potentials for Downstream Separation of 1,3-Propanediol", Biotechnology Techniques, vol. 18, No. 2 (Jan. 1, 1999), pp. 127-130.
Cox et al. "Mechanistic Studies in Strong Acids . . . ", Journal of Organic Chemistry, vol. 51, No. 19 (Sep. 1, 1986), pp. 3619-3624.
Li et al. "Aqueous Two-phase Extraction of 1,3-propanediol from Glycerol-based Fermentation Broths", Separation and Purification Technology Separation and Purification Technology, vol. 66, No. 3 (May 7, 2009), pp. 472-478.
USPTO Notice of Allowance for U.S. Appl. No. 13/431,358 dated Aug. 2, 2013.
USPTO Notice of Allowance for U.S. Appl. No. 12/889,045 dated Sep. 19, 2013.
USPTO Notice of Allowance for U.S. Appl. No. 13/896,706 dated Oct. 4, 2013.
USPTO Office Action for U.S. Appl. No. 13/431,358 dated Nov. 12, 2013.

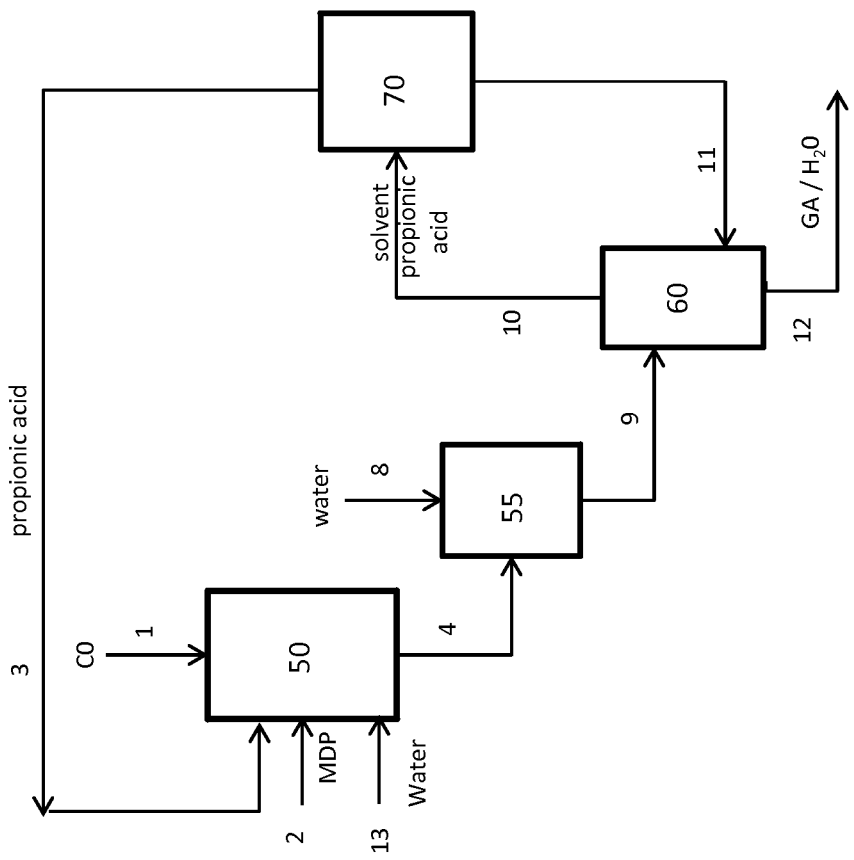

HYDROCARBOXYLATION OF METHYLENE DIPROPIONATE IN THE PRESENCE OF PROPIONIC ACID AND A HETEROGENEOUS CATALYST

FIELD OF THE INVENTION

This invention relates to a process for the production and purification of glycolic acid or glycolic acid derivatives by the carbonylation of methylene dipropionate in the presence of a solid acid catalyst and propionic acid. This invention discloses hydrocarboxylations and corresponding glycolic acid separations wherein the propionic acid stream is readily removed from the glycolic acid and the propionic acid is recycled.

BACKGROUND OF THE INVENTION

Glycolic acid (also known as 2-hydroxyacetic acid or α-hydroxyacetic acid) can be used for many purposes including as a raw material to make ethylene glycol. Glycolic acid is prepared by the acid catalyzed reaction of carbon monoxide and formaldehyde in the presence of water, alcohols, and/or carboxylic acids. These processes often require high temperatures and pressures to proceed at practical rates. For example, glycolic acid typically is prepared by reacting formaldehyde with carbon monoxide and water in the presence of an acidic catalyst such as sulfuric acid under high temperature and pressure such as, for example, above 480 bar absolute (abbreviated herein as "bara"), and between 200 and 225° C. Alternatively, lower pressures may be employed in the presence of hydrogen fluoride as a catalyst and solvent. These processes, however, require expensive materials of construction and/or recovery and recycling schemes for hydrogen fluoride. Furthermore, readily available formaldehyde starting material typically contains large concentrations of water that inhibit the rate of the carbonylation reaction. Aqueous formaldehyde also is present as a mixture of formaldehyde and oligomers and polymers of formaldehyde which does not allow accurate control of feed mole ratios (e.g. moles of water per mole of formaldehyde equivalents). The alternative of using dry formaldehyde entails the materials handling difficulty of feeding a solid reactant. Furthermore, formaldehyde in the feed readily breaks down to formic acid causing yield loss and making purification of the glycolic acid product difficult. Thus, there is a need for an alternative to the aqueous formaldehyde feed or dry formaldehyde feed (e.g., paraformaldehyde or trioxane) in the process for making glycolic acid that can be accomplished at moderate temperatures and pressures and allows for the ready separation of the glycolic acid from the crude hydrocarboxylation reactor product.

SUMMARY OF THE INVENTION

The present invention provides in one embodiment a process for the preparation of glycolic acid, comprising
 (A) feeding carbon monoxide, methylene dipropionate, propionic acid, and water to a hydrocarboxylation reaction zone comprising a solid acid catalyst to produce an effluent comprising esters of glycolic and propionic acids;
 (B) hydrolyzing the effluent to produce a hydrolyzed mixture comprising glycolic acid and the propionic acid;
 (C) recovering the propionic acid from the hydrolyzed mixture by extracting the hydrolyzed mixture with a hydrophobic solvent selected from at least one of the group consisting of esters having from 4 to 20 carbon atoms, ethers having from 4 to 20 carbon atoms, ketones having from 4 to 20 carbon atoms, and hydrocarbons having from 6 to 20 carbon atoms to form an aqueous raffinate phase comprising a major amount of the glycolic acid contained in the hydrolyzed mixture and an organic extract phase comprising a major amount of the propionic acid contained in the hydrolyzed mixture; and
 (D) separating the aqueous raffinate phase and the organic extract phase.

The present invention provides in another embodiment a process for the preparation of glycolic acid, comprising
 (A) feeding carbon monoxide, methylene dipropionate, propionic acid, and water to a hydrocarboxylation reactor zone comprising a solid acid catalyst to produce an effluent comprising esters of glycolic and propionic acids;
 (B) hydrolyzing the effluent to produce a hydrolyzed mixture comprising glycolic acid and the propionic acid;
 (C) recovering the propionic acid from the hydrolyzed mixture by extracting the hydrolyzed mixture with a hydrophobic solvent selected from at least one of the group consisting of n-propyl acetate, i-propyl acetate, n-butyl acetate, i-butyl acetate, s-butyl acetate, methyl propionate, ethyl propionate, i-propyl propionate, methyl tertiary-butyl ether, methyl i-butyl ketone, methyl i-propyl ketone, methyl propyl ketone, and toluene to form an aqueous raffinate phase comprising a major amount of the glycolic acid contained in the hydrolyzed mixture and an organic extract phase comprising a major amount of the propionic acid contained in the hydrolyzed mixture; and
 (D) separating the aqueous raffinate phase and the organic extract phase.

DESCRIPTION OF THE DRAWINGS

FIG. 1 is a schematic of an embodiment of the present invention for hydrocarboxylation of methylene dipropionate.

DETAILED DESCRIPTION

The present invention provides in a first embodiment a process for the preparation of glycolic acid, comprising
 (A) feeding carbon monoxide, methylene dipropionate, propionic acid, and water to a hydrocarboxylation reaction zone comprising a solid acid catalyst to produce an effluent comprising esters of glycolic and propionic acids;
 (B) hydrolyzing the effluent to produce a hydrolyzed mixture comprising glycolic acid and the propionic acid;
 (C) recovering the propionic acid from the hydrolyzed mixture by extracting the hydrolyzed mixture with a hydrophobic solvent selected from at least one of the group consisting of esters having from 4 to 20 carbon atoms, ethers having from 4 to 20 carbon atoms, ketones having from 4 to 20 carbon atoms, and hydrocarbons having from 6 to 20 carbon atoms to form an aqueous raffinate phase comprising a major amount of the glycolic acid contained in the hydrolyzed mixture and an organic extract phase comprising a major amount of the propionic acid contained in the hydrolyzed mixture; and
 (D) separating the aqueous raffinate phase and the organic extract phase.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

It is to be understood that the mention of one or more process steps does not preclude the presence of additional process steps before or after the combined recited steps or intervening process steps between those steps expressly identified. Moreover, the lettering of process steps or ingredients is a convenient means for identifying discrete activities or ingredients and the recited lettering can be arranged in any sequence, unless otherwise indicated.

As used herein the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The term "glycolic acid", as used herein, refers to the chemical compound, glycolic acid, also known as 2-hydroxyacetic acid. The term "glycolic acid oligomers", as used herein, refers to the reaction products of glycolic acid with itself, particularly the linear or cyclic esters formed by a reaction between the carboxyl group of one molecule and the alcohol group of another molecule. The "glycolic acid oligomers" include, but are not limited to, (2-hydroxyacetoxy) acetic acid (G2), 2-(2'-hydroxyacetoxy)acetoxyacetic acid (G3), and 2-(2'-(2"-hydroxyacetoxy)acetoxy)acetoxyacetic acid (G4). The term "esters of glycolic and propionic acids", as used herein, refers to the esters produced by the reaction of a propionic acid with the hydroxyl end of glycolic acid and/or its oligomers.

The term "methylene dipropionate", as used herein, refers to the chemical compound known to those skilled in the art. "Methylene dipropionate" has one "formaldehyde equivalent." The term "formaldehyde equivalent" as used herein, refers to the compounds propensity in the hydrocarboxylation reaction to make glycolic acid, glycolic acid oligomers or esters of glycolic acid and carboxylic acids or combinations thereof. Each mole of methylene dipropionate is one formaldehyde equivalent as one mole of glycolic acid is produced for each mole of methylene dipropionate. Other examples of formaldehyde equivalents, include but are not limited to, methylene diacetate (one formaldehyde equivalent), formalin (one formaldehyde equivalent) and 1,3,5-trioxane (three formaldehyde equivalents).

The term "hydrocarboxylation reaction zone", as used herein, refers to the part of the process wherein the carbon monoxide, methylene dipropionate, propionic acid, and water are fed, a solid acid catalyst is fed to or contained therein, and esters of glycolic and propionic acids are produced. The term "effluent", as used herein, refers to the liquid stream exiting the hydrocarboxylation reaction zone comprising the "esters of glycolic and propionic acids".

The term "hydrolyzing", as used herein, refers to reacting with water. The term "hydrolyzed mixture", as used herein, refers to the effluent from a hydrocarboxylation reaction zone after "hydrolyzing" it; the "hydrolyzed mixture" comprises glycolic acid and propionic acid.

The term "extracting", as used herein, refers to separating a component from a feed into an immiscible liquid based upon relative differences in solubility. As used herein, the term "feed" is intended to have its commonly understood meaning in the liquid-liquid extraction art, which is the solution that contains the materials to be extracted or separated. The term "extraction solvent", as used herein, is intended to be synonymous with the term "extractant" or "solvent" and is intended to mean the immiscible liquid that is used in the extraction process to extract materials or solutes from the feed. The term "extract" is the immiscible liquid left from the extraction solvent after it has been contacted with the feed. The term "raffinate" is intended to mean the liquid phase left from the feed after it has been contacted with the extraction solvent. The term "wash solvent" is understood to mean a liquid used to wash or enhance the purity of the raffinate or extract phase.

The term "hydrophobic solvent", as used herein, refers to a solvent that will phase separate when mixed with water. The "hydrophobic solvent" is synonymous with the extractant solvent for the present invention. In the present invention, examples of hydrophobic solvents are "esters", "ethers", "ketones", and "hydrocarbons" which are terms well known to those skilled in the art. In the present invention, the extraction produces an organic extract phase and an aqueous raffinate phase. The term a "major amount", as used herein, for example "a major amount of the glycolic acid contained in the hydrolyzed mixture" refers to at least 50 weight percent of the glycolic acid contained in the hydrolyzed mixture. In a further example, when a raffinate phase comprises a major amount of the glycolic acid contained in the hydrolyzed mixture, the weight of the glycolic acid in the raffinate phase divided by the weight of the glycolic acid contained in the hydrolyzed mixture is at least 50 weight percent. The term a "minor amount", as used herein, for example "a minor amount of glycolic acid contained in the hydrolyzed mixture" refers to less than 50 weight percent of the glycolic acid contained in the hydrolyzed mixture. The term "hydrophilic solvent", as used herein, refers to a solvent that is miscible with water.

The term "molar ratio", as used herein, refers to the moles of one component divided by the moles of another component. For example, if the molar ratio of propionic acid to methylene dipropionate is 2:1, then for every mole of methylene dipropionate, there are two moles of propionic acid. Each mole of methylene dipropionate can be considered as one mole of formaldehyde equivalent in the hydrocarboxylation reaction.

The terms "reactions of ethylene glycol and glycolic acid", and "reacting ethylene glycol and glycolic acid", and "reacting ethylene glycol with an aqueous raffinate phase" which comprises glycolic acid, as used herein, refer to the many reactions that occur when ethylene glycol and glycolic acid are present at typical reaction conditions. The reactions include reactions between ethylene glycol and glycolic acid and reactions of glycolic acid with itself. Additionally, the reactions include reactions between ethylene glycol, glycolic acid, and glycolic acid oligomers or other reaction products such as 2-hydroxyethyl 2-hydroxyacetate. The term "glycolate ester oligomers", as used herein, refers to the many reaction products of glycolate esters formed by "reacting ethylene glycol and glycolic acid". Examples include, but are not limited to, 2-hydroxyethyl 2-hydroxyacetate, 1,2-ethanediyl bis(2-hydroxyacetate), 2'-[2"-(2'"-hydroxyacetoxy)acetoxy] ethyl 2-hydroxyacetate, 2'-(2"-[2'"-(2""-hydroxyacetoxy)acetoxy]acetoxy)ethyl 2-hydroxyacetate, 2"-hydroxyethyl (2'-hydroxyacetoxy)acetate, 2"-hydroxyethyl 2'-(2"-hydroxyacetoxy)acetoxyacetate, and 2""-hydroxyethyl 2'-[2"-(2'"-hydroxyacetoxy)acetoxy]acetoxyacetate.

Methylene dipropionate can be produced by the reaction of propionic anhydride with formaldehyde. To improve yields of the reaction, the formaldehyde is preferably dry. The formaldehyde can be trioxane or paraformaldehyde and linear oligomers and polymers of formaldehyde, i.e., poly(oxymethylene) glycols and derivatives thereof, formed from the polymerization or oligomerization of formaldehyde in water or other solvents. The term "formaldehyde", as used herein, is intended to include all the various forms of formaldehyde described above. The reaction can take place using an acidic catalyst such as sulfuric acid, trifluoromethanesulfonic acid (also known as triflic acid), methanesulfonic acid, and the like. The reaction can take place at a temperature of from 40 to 180° C. and at a pressure of from 0.1 bar gauge to 10 bar gauge. Methylene dipropionate can be purified by distillation.

In the process of the present invention, the propionic acid serves as a solvent and promoter for the hydrocarboxylation reaction. The propionic acid will react in the hydrocarboxylation reaction zone to form 2-propionoxyacetic acid. The 2-propionoxyacetic acid is hydrolyzed to produce glycolic acid and the propionic acid.

In the process of the present invention the molar ratio of propionic acid to methylene dipropionate (propionic acid:methylene dipropionate) fed to the hydrocarboxylation zone can vary over a considerable range. Examples include feeding at a propionic acid:methylene dipropionate of from 0.01:1 to 10:1, or 0.01:1 to 6:1, or 0.01:1 to 3:1, or 0.01:1 to 2:1, or 0.01:1 to 1:1, 0.05:1 to 10:1, or 0.05:1 to 6:1, or 0.05:1 to 3:1, or 0.05:1 to 2:1, or 0.05:1 to 1:1, or 0.1:1 to 10:1, or 0.1:1 to 6:1, or 0.1:1 to 3:1, or 0.1:1 to 2:1, or 0.1:1 to 1:1.

In the process of the present invention the molar ratio of water to methylene dipropionate (water:methylene dipropionate) fed to the hydrocarboxylation zone can vary over a considerable range. Examples include feeding at a water:methylene dipropionate of from 0.25:1 to 2:1, or 0.25:1 to 1.5:1, or 0.25:1 to 1:1, or 0.25:1 to 0.8:1, or 0.50:1 to 2:1, 0.5:1 to 1.5:1, or 0.5:1 to 1:1, or 0.5:1 to 0.8:1, or 0.8:1 to 2:1, or 0.8:1 to 1.5:1, or 0.8:1 to 1:1, or 1:1 to 2:1, or 1:1 to 1.5:1. In another aspect the water:methylene dipropionate is 1:1.

The hydrocarboxylation process can be carried out by feeding carbon monoxide to a reaction mixture comprising methylene dipropionate in the presence of a solid acid catalyst. The carbon monoxide typically is supplied to the reaction mixture in sufficient excess to insure an adequate supply thereof for absorption by the reaction mixture. The amount of carbon monoxide useful for the carbonylation reaction ranges from a molar ratio of 1:1 to 1,000:1 or 1:1 to 100:1 or 1:1 to 20:1 or 1:1 to 20:1 or 2:1 to 20:1 or 2:1 to 10:1 of carbon monoxide to formaldehyde equivalents.

The composition of the carbon monoxide stream required for hydrocarboxylation may comprise carbon monoxide, hydrogen, and carbon dioxide. For example, the carbon monoxide may be supplied in substantially pure form or as a mixture with other gases such as, for example, hydrogen, carbon dioxide, methane, nitrogen, noble gases (e.g., helium and argon), and the like. For example, the carbon monoxide need not be of high purity and may contain from 1% by volume to 99% by volume carbon monoxide. The remainder of the gas mixture may include such gases as, for example, nitrogen, hydrogen, water, carbon dioxide, noble gases, and paraffinic hydrocarbons having from one to four carbon atoms. In order to reduce compression costs, it is desirable for the carbon monoxide stream to comprise at least 95 mole % carbon monoxide, more preferably at least 99 mole %.

The carbon monoxide may be obtained from typical sources that are well known in the art. For example, the carbon monoxide may be provided by any of a number of methods known in the art including steam or carbon dioxide reforming of carbonaceous materials such as natural gas or petroleum derivatives; partial oxidation or gasification of carbonaceous materials, such as petroleum residuum, bituminous, sub bituminous, and anthracitic coals and cokes; lignite; oil shale; oil sands; peat; biomass; petroleum refining residues of cokes; and the like. For example, the carbon monoxide may be provided to the reaction mixture as a component of synthesis gas or "syngas", comprising carbon dioxide, carbon monoxide, and hydrogen.

The hydrocarboxylation process can be conducted under continuous, semi-continuous, and batch modes of operation and may utilize a variety of reactor types. Examples of suitable reactor types include, but are not limited to, stirred tank, continuous stirred tank, trickle bed, tower, slurry, and tubular reactors. A typical temperature range for the hydrocarboxylation reaction is from 80 to 220° C. Other examples of the temperature range are from 80 to 210° C., 80 to 200° C., 80 to 190° C., 90 to 220° C., 90 to 210° C., 90 to 200° C., 90 to 190° C., 100 to 220° C., 100 to 210° C., 100 to 200° C., 100 to 190° C., 110 to 210° C., 110 to 200° C., 110 to 190° C., 120 to 220° C., 120 to 210° C., 120 to 200° C., 140 to 220° C., 140 to 210° C., or 150 to 210° C. Examples of pressure ranges for the hydrocarboxylation reaction are 35 to 250 bar gauge, 35 to 200 bar gauge, and 60 to 200 bar gauge. In one example of the process, carbon monoxide, methylene dipropionate, propionic acid, and water are fed at a molar ratio of carbon monoxide to methylene dipropionate ranging from 1:1 to 10:1, and the hydrocarboxylation reaction zone is operated at a pressure of from 35 bar gauge to 200 bar gauge and a temperature of from 80° C. to 220° C.

The hydrocarboxylation reactants may be introduced separately or in any sequence or combination to the hydrocarboxylation reaction zone. In addition, one or more reactants may be introduced at different locations in the reactor. For example, in a continuously operated process containing a catalyst bed in a reactor, the addition of water or methylene dipropionate may be staged throughout the reactor. In some cases, it may be desirable to recirculate a portion of the reaction media to the reactor to act as a liquid reaction media for the next synthesis. In order to reduce by-product formation, it is desirable to set the residence time in the hydrocarboxylation reaction zone to give an outlet formaldehyde equivalent concentration of 5 weight percent or less. In addition to glycolic acid, the hydrocarboxylation process typically produces glycolic acid oligomers, water, and unreacted methylene dipropionate or formaldehyde equivalents. When propionic acid is present, the hydrocarboxylation process typically also produces esters of glycolic and propionic acids.

The advantages of using solid acid catalysts in the hydrocarboxylation reaction include being able to readily separate the reaction product and catalyst by mechanical means. The liquid phase reaction of carbon monoxide and methylene dipropionate is promoted by using certain solid phase, insoluble particulate catalyst materials. The term "insoluble" as used herein means that the catalyst is substantially insoluble in any combination of reactants or reaction products under reaction conditions present in the practice of hydrocarboxylation. The description of the catalyst as "particulate" refers to its size being such that it is separable from a liquid medium by simple means. Typical catalyst particle diameters are 2.0 to 0.001 millimeters.

In general, substances capable of forming Lewis or Brønsted type acids are useful catalysts. Examples of solid acids include strong acid cation exchange resins, solidified acids, clay minerals, zeolites, inorganic oxides and composite oxides. They are characterized in having their acid function available on a solid surface without releasing acidity into the liquid reaction medium. The acidity required of materials useful as catalysts in the practice of this invention may be measured as hydrogen ion exchange capacity. Although the catalysts or process of the present invention are not based on any theory of ion-exchange, it is useful to define the acidity criteria of acceptable solid catalysts as those which have hydrogen ion-exchange capacity of at least 0.1 milliequivalents per gram.

Strong acid type cation-exchange resins in hydrogen form are useful catalysts in the practice of hydrocarboxylation. Illustrative resins are those strong acid types having sulfonic acid functionality. The strong acid moiety may be pendant to a variety of polymeric backbones such as styrene-divinylbenzene or tetrafluoroethylene. The choice of polymeric backbone will depend on a variety of factors such as cost and temperature resistance. For instance, AMBERLYST resins produced by Rohm & Haas, Inc. are sulfonated styrene-divinylbenzene with increasing degrees of crosslinking corresponding to higher divinylbenzene content: AMBERLYST 15, 36 and 70 have maximum recommended operating temperatures of 120, 150 and 190° C., respectively. SMOPEX resins, offered by Johnson Matthey are sulfonic acid resins with a polyethylene backbone. SMOPEX 101 with 4%, 8% and 12% crosslinking have maximum operating temperatures of 160-190° C. NAFION resins offered by DuPont Inc. are sulfonated resins with fluorinated polymer backbones, providing very high acidity and chemical resistance. NAFION 50 has a maximum recommended operating temperature of 160° C.

Solid acids may also be composed of strongly acidic materials deposited on a robust support such as SAC-13 offered by BASF which contains 13% NAFION supported on silica. Likewise, Johnson Matthey offers 20% tungsten/silica which is a dicesium phosphotungstic acid (a heteropolyacid: $Cs_2HPW_{12}O_{40}$) supported on silica.

Examples of the clay minerals and zeolites include montmorillonite, kaolinite, bentonite, halloysite, smectite, illite, vermiculite, chlorite, sepiolite, attapulgite, palygorskite and mordenite. In particular, among these clay minerals and zeolites, preferred are those treated with an acid such as hydrogen fluoride, or those obtained by replacing a replaceable metal ion of these clay minerals and zeolites with a hydrogen ion such as H-type zeolite. Süd-Chemie offers K10 catalyst which is an example of an activated clay and has been demonstrated in this work.

In one example, the solid acid catalyst is selected from at least one of the group consisting of sulfonic acid resins, silica-aluminate, silica-alumino-phosphates, heteropolyacids, supported heteropolyacids, sulfuric acid treated metal oxides, and phosphoric acid treated metal oxides. Examples in addition to the specific commercially available catalysts above include the following. Examples of sulfonic acid resins include, but are not limited to, sulfonic acid resins of at least one of the group selected from polystyrene, polyethylene, fluorinated polymers, brominated polystyrene, chlorinated polystyrene, and fluorinated polystyrene. Examples of silica-aluminates include, but are not limited to, Zeolites such as pentasils, faujasites, chabazites, mordenites, offretites, stilbites, clinoptolites, natrolites, and the like. Examples of silica-alumino-phosphates include, but are not limited to, SAPO-5 and SAPO-34. The heteropolyacid comprises metal addenda atoms, such as tungsten, molybdenum, or vanadium, linked by oxygen atoms form a hetero-atom-centered cluster bonded via oxygen atoms. The hetero-atom is selected generally from the p-block of the periodic table, such as silicon, phosphorus, or arsenic. Examples of heteropolyacid structure are Keggin, $H_nXM_{12}O_{40}$, and Dawson, $H_nX_2M_{18}O_{62}$, type clusters, such as, but not limited to $H_4X^{n+}M_{12}O_{40}$, wherein X=Si, Ge and M=Mo, W; $H_3X^{n+}M_{12}O_{40}$, wherein X=P, As and M=Mo, W; and $H_6X_2M_{18}O_{62}$, wherein X=P, As and M=Mo, W. Examples of supported heteropolyacids include, but are not limited to, $H_3PMo_{12}O_{40}$ on silica, $H_3PW_{12}O_{40}$ on silica, and $H_4SiW_{12}O_{40}$ on silica. Examples of sulfuric acid treated metal oxides include, but are not limited to, $SiO_2$ treated with sulfuric acid, $TiO_2$ treated with sulfuric acid, $ZrO_2$ treated with sulfuric acid, and $TiO_2/MoO_2$ mixed metal oxide treated with sulfuric acid. Examples of phosphoric acid treated metal oxides include, but are not limited to, niobium oxide treated with phosphoric acid and tungsten oxide treated with phosphoric acid.

In general, the rate of reaction increases with increasing catalyst concentration. Because solid catalysts are easily separated from the reaction mixture, they can be used at higher levels to achieve shorter reaction times, lower temperatures, or lower pressures. Although the catalyst may be present in amounts as low as to provide a minimum of 0.01 mole of hydrogen ion per mole of formaldehyde equivalent, greater proportions of catalyst, approaching or exceeding one mole of hydrogen ion per mole of formaldehyde equivalent, can be used to achieve higher reaction rates. In one embodiment of the process of the invention, for example, the process can be operated as a continuous process in which the maximum allowable catalyst concentration is limited only by the weight of catalyst which may be packed into the volume of the hydrocarboxylation reaction zone while preserving effective contact of reactants and practical flow rates.

In the process of the present invention, an effluent comprising esters of glycolic and propionic acids is produced in the hydrocarboxylation reaction zone. The esters of glycolic and propionic acids are produced by the reaction of a propionic acid with the hydroxyl end of glycolic acid and/or its oligomers. The esters of glycolic and propionic acids comprise 2-propionoxyacetic acid, (2'-propionyloxy)acetoxyacetic acid, or mixtures thereof.

The effluent from the hydrocarboxylation reaction zone may be hydrolyzed by means known to one skilled in the art. Typically, water will be added to the effluent in an excess of the amount needed to react with the esters of glycolic and propionic acids to produce a hydrolyzed mixture comprising glycolic acid and propionic acid. The glycolic acid oligomers react with water to form glycolic acid and the 2-propionoxyacetic acid and (2'-propionyloxy)acetoxyacetic acid react with water to form propionic acid and glycolic acid.

The composition of the hydrolyzed mixture can vary. While an increase in the amount of water may improve hydrolysis rates, the additional water must be separated from the glycolic acid. In one example, the molar ratio of water to glycolic acid in the resulting hydrolyzed mixture (water:glycolic acid) is from 1:1 to 15:1. Other examples of water:glycolic acid are from 1:1 to 8:1, or 1:1 to 6:1, or 1:1 to 4:1, or 1.5:1 to 15:1, or 1.5:1 to 8:1, or 1.5:1 to 6:1, or 1.5:1 to 4:1, or 2:1 to 15:1, or 2:1 to 8:1, or 2:1 to 6:1, or 2:1 to 4:1.

In the process of the present invention, the propionic acid is recovered by extracting the hydrolyzed mixture with a hydrophobic solvent with the glycolic acid partitioning to the raffinate. The hydrophobic solvent can be selected from esters having from 4 to 20 carbon atoms, ethers having from 4 to 20 carbon atoms, ketones having from 4 to 20 carbon atoms, and hydrocarbons having from 6 to 20 carbon atoms. In one aspect of the invention, the hydrophobic solvent comprises ethyl acetate, n-propyl acetate, i-propyl acetate, n-butyl acetate, i-butyl acetate, s-butyl acetate, methyl benzoate, i-butyl isobutyrate, 2-ethylhexyl acetate, cyclohexyl acetate, methyl propionate, ethyl propionate, n-propyl propionate, i-propyl propionate, i-butyl propionate, n-butyl propionate, s-butyl propionate, diethyl ether, dipropyl ether, diisopropyl ether, dibutyl ethers, methyl tertiary-butyl ether, methyl tertiary-amyl ether, methyl ethyl ketone, methyl i-butyl ketone, methyl i-propyl ketone, methyl propyl ketone, dibutyl ketone, diisobutyl ketone, isophorone, 3,3,5-trimethylcyclohexanone, cyclohexanone, 2-heptanone, methyl-iso-amyl ketone, diethyl ketone, 5-ethyl 2-nonanone, diamyl ketone, diisoamyl ketone, heptane, hexane, toluene, or mixtures thereof. In another aspect of the invention, the hydrophobic solvent comprises n-propyl acetate, i-propyl acetate, n-butyl acetate, i-butyl acetate, s-butyl acetate, methyl propionate, ethyl propionate, i-propyl propionate, methyl tertiary-butyl ether, methyl i-butyl ketone, methyl i-propyl ketone, methyl propyl ketone, toluene, or mixtures thereof. In yet another aspect of the invention, the hydrophobic solvent comprises n-propyl acetate, i-propyl acetate, methyl propionate, ethyl propionate, i-propyl propionate, methyl tertiary-butyl ether, methyl i-butyl ketone, or mixtures thereof.

The process of the present invention forms an aqueous raffinate phase comprising a major amount of glycolic acid and a minor amount of propionic acid contained in the hydrolyzed mixture. In an aspect of the invention, greater than 80 weight percent of the glycolic acid in the hydrolyzed mixture is recovered in the raffinate phase. In another aspect, greater than 90 weight percent, greater than 95 weight percent, greater than 98 weight percent, greater than 99 weight percent, or greater than 99.5 weight percent of the glycolic acid in the hydrolyzed mixture is recovered in the aqueous raffinate phase.

The process of the present invention forms an organic extract phase comprising a major amount of the propionic acid and a minor amount of the glycolic acid. In an aspect of the invention greater than 90 weight percent of the propionic acid in the hydrolyzed mixture is recovered in the organic extract phase. In another aspect, greater than 95 weight percent, greater than 98 weight percent, or greater than 99 weight percent, or greater than 99.5 weight percent, or greater than 99.9 weight percent of the propionic acid in the hydrolyzed mixture is recovered in the organic extract phase.

Extracting the hydrolyzed mixture can be carried out by any means known in the art to intimately contact two immiscible liquid phases and to separate the resulting phases after the extraction procedure. For example, the extraction can be carried out using columns, centrifuges, mixer-settlers, and miscellaneous devices. Some representative examples of extractors include unagitated columns (e.g., spray, baffle tray and packed, perforated plate), agitated columns (e.g., pulsed, rotary agitated, and reciprocating plate), mixer-settlers (e.g., pump-settler, static mixer-settler, and agitated mixer-settler), centrifugal extractors (e.g., those produced by Robatel, Luwesta, deLaval, Dorr Oliver, Bird, CINC, and Podbielniak), and other miscellaneous extractors (e.g., emulsion phase contactor, electrically enhanced extractors, and membrane extractors). A description of these devices can be found in the "Handbook of Solvent Extraction", Krieger Publishing Company, Malabar, Fla., 1991, pp. 275-501. The various types of extractors may be used alone or in any combination.

The extraction may be conducted in one or more stages. The number of extraction stages can be selected in consideration of capital costs, achieving high extraction efficiency, ease of operability, and the stability of the hydrolyzed mixture and extraction solvents to the extraction conditions. The extraction also can be conducted in a batch or continuous mode of operation. In a continuous mode, the extraction may be carried out in a co-current, a counter-current manner, or as a fractional extraction in which multiple solvents and/or solvent feed points are used to help facilitate the separation. The extraction process also can be conducted in a plurality of separation zones that can be in series or in parallel.

The extraction typically can be carried out at a temperature of 10 to 120° C. For example, the extraction can be conducted at a temperature of 30 to 80° C. The desired temperature range may be constrained further by the boiling point of the extractant components or water. Generally, it is undesirable to operate the extraction under conditions where the extractant boils. In one aspect, the extractor can be operated to establish a temperature gradient across the extractor in order to improve the mass transfer kinetics or decantation rates. In another aspect, the extractor may be operated under sufficient pressure to prevent boiling.

In an aspect of the invention, the hydrolyzed mixture is extracted in a continuous counter-current extractor. The hydrophobic solvent is fed to the extractor at a location lower than the feed location of the hydrolyzed mixture. The hydrophobic solvent moves up the counter-current extractor to form an organic extract phase exiting the top of the extractor and comprising a major amount of the propionic acid and a minor amount of the glycolic acid contained in the hydrolyzed mixture. The hydrolyzed mixture moves down the counter-current extractor to form an aqueous raffinate phase exiting the bottom of the extractor and comprising a major amount of the glycolic acid and a minor amount of the propionic acid contained in the hydrolyzed mixture. In an aspect of the invention the feed ratio of the hydrophobic solvent to the hydrolyzed mixture on a weight basis ranges from 0.1:1 to 20:1, or 0.1:1 to 10:1, or 0.1:1 to 5:1, or 0.1:1 to 4:1, or 0.5:1 to 20:1, or 0.5:1 to 10:1, or 0.5:1 to 5:1, or 0.5:1 to 4:1, or 1:1 to 10:1, or 1:1 to 5:1, or 1:1 to 4:1.

The hydrolyzed mixture and hydrophobic solvent can be contacted by fractional extraction methods such as, for example, by fractional counter-current extraction. As used herein, the term "fractional counter-current extraction" is intended to include, but is not limited to, a method for separating a feed stream, e.g., hydrolyzed mixture, containing two or more substances by charging the feed stream to a counter-current extraction process between the points where two immiscible solvents are charged to the extraction process. The two immiscible solvents should be immiscible over the entire temperature range of the extraction process. This method is sometimes referred to as "double solvent extraction." Fractional counter-current extraction can involve the use of a cascade of stages, extracting solvents and solution to be extracted entering at opposite ends of the cascade with the feed phase and hydrophobic extractant phase flowing counter-currently. Some example fractional counter-current extraction configurations may be found in Treybal, *Liquid Extraction*, 2nd Edition, McGraw-Hill Book Company, New York. 1963, pp. 275-276.

In an aspect of the invention, the hydrolyzed mixture is extracted in a continuous fractional counter-current extractor. The hydrophobic solvent is fed to the extractor at a location lower than the feed location of the hydrolyzed mixture. A hydrophilic solvent is fed to the extractor at a location higher than the hydrolyzed mixture. In an aspect of the invention the feed ratio of the hydrophobic solvent to the hydrolyzed mixture on a weight basis ranges from 0.5:1 to 20:1, or 1:1 to 10:1, or 1:1 to 5:1 and the feed ratio of the hydrophilic solvent to the hydrolyzed mixture on a weight basis ranges from 0.01:1 to 5:1, or 0.05:1 to 2:1, or 0.1:1 to 1.5:1, or 0.1:1 to 0.8:1. In one example, the hydrophilic solvent comprises water. In another example, the hydrophilic solvent comprises water and ethylene glycol. In another example, the hydrophilic solvent comprises 50 weight percent to 100 weight percent water and 0 weight percent to 50 weight percent ethylene glycol, each on a total hydrophilic solvent weight basis.

In the process of the present invention, the extracting of the hydrolyzed mixture results in an aqueous raffinate phase comprising a major amount of the glycolic acid and a minor amount of the propionic acid contained in the hydrolyzed mixture and an organic extract phase comprising a major amount of the propionic acid and a minor amount of the glycolic acid contained in the hydrolyzed mixture. The raffinate phase and the extract phase may be separated by any phase separation technology known in the art. The phase separation techniques can be accomplished in the extractor or in a separate liquid-liquid separation device. Suitable liquid-liquid separation devices include, but are not limited to, coalescers, cyclones and centrifuges. Typical equipment that can be used for liquid-liquid phase separation devices are described in the *Handbook of Separation Process Technology*, ISBN 0-471-89558-X, John Wiley & Sons, Inc., 1987.

One aspect of the process of the present invention further comprises (E) separating the organic extract phase into the hydrophobic solvent and propionic acid, recycling the hydrophobic solvent to step (C), and recycling the propionic acid to step (A). The hydrophobic solvent and propionic acid can be separated by any means known to one skilled in the art. Examples include by distillation and extraction. In one example, the hydrophobic solvent has a lower boiling point than propionic acid and the two components are separated via distillation. The hydrophobic solvent is recovered as the distillate product and recycled for extracting in step (C) and the propionic acid is the bottom product and recycled to the hydrocarboxylation reaction zone in step (A). In another example, the hydrophobic solvent has a higher boiling point than the propionic acid and the two components are separated via distillation. The hydrophobic solvent is recovered as the bottom product and recycled for extracting in step (C) and the propionic acid is the distillate product and recycled to the hydrocarboxylation reaction zone in step (A).

One aspect of the process of the present invention further includes (F) reacting a first ethylene glycol with the aqueous raffinate phase while simultaneously removing water to produce an esterification effluent comprising glycolate ester oligomers and glycolic acid oligomers and an overhead stream comprising water; and (G) reacting hydrogen with the esterification effluent to produce a second ethylene glycol, separating the second ethylene glycol into a product ethylene glycol and the first ethylene glycol, and recycling the first ethylene glycol to step (F). The reaction between the first ethylene glycol and the glycolic acid of the aqueous raffinate phase and simultaneous removal of water can be conducted under standard esterification conditions known to persons skilled in the art. Part of the water in the aqueous raffinate phase can be removed prior to esterification. For example, the esterification can be achieved by adding hot ethylene glycol to the aqueous raffinate phase and removing water formed during esterification until sufficient water is removed and an esterification effluent comprising glycolate ester oligomers and glycolic acid oligomers is formed. Typically excess ethylene glycol is used to ensure complete esterification. Examples of mole ratios of ethylene glycol to glycolic acid vary from 0.25:1 to 10:1 or 0.25:1 to 6:1 or 0.25 to 3:1 or 0.5:1 to 10:1 or 0.5:1 to 6:1 or 0.5:1 to 3:1 or 1:1 to 10:1 or 1:1 to 6:1 or 1:1 to 3:1 or 1.5:1 to 10:1 or 1.5:1 to 6:1 or 1.5:1 to 3:1 or 2:1 to 10:10 or 2:1 to 6:1. Representative conditions for esterification include at a temperature of from 150 to 250° C., preferably from 170 to 220° C., and a pressure of from 1 bara to 8 bara, preferably from 1 bara to 5 bara.

The esterification effluent can be hydrogenated to produce ethylene glycol by contacting the glycolate ester oligomers and glycolic acid oligomers with hydrogen in the presence of a suitable hydrogenation catalyst. The hydrogenation reaction can be conducted in the liquid or the gas phase using known processes. Typically, glycolate ester oligomers and glycolic acid oligomers are contacted with hydrogen under pressure in the presence of a catalyst effective for hydrogenation at temperatures from 150 to 300° C. Additional examples of temperatures ranges are from 200 to 250° C. Examples of typical pressure ranges are from 35 bara to 350 bara and 70 bara to 140 bara. Considerable latitude in the temperature and pressure of hydrogenation is possible depending upon the use and choice of hydrogenation catalyst and whether the process is conducted in the liquid or gas phase.

The hydrogenation catalyst may comprise any metal or combination of metals effective for the hydrogenation of esters to alcohols. Typical hydrogenation catalysts include, but are not limited to, at least one metal selected from Groups 8, 9, 10 of the Periodic Table of the Elements (1984 Revision by IUPAC), and copper. In addition, the hydrogenation catalyst may comprise at least one additional metal promoter selected from chromium, magnesium, barium, sodium, nickel, silver, lithium, potassium, cesium, zinc, cobalt, and gold. The term "metal", as used herein in the context of hydrogenation catalysts, is understood to include metals in their elemental form and compounds thereof such as, for example, metal oxides, salts, and complexes with organic ligands. For example, the hydrogenation catalyst can comprise a Raney nickel or a metal oxide. Typical metal oxide catalysts include, for example, copper chromite, copper oxide, or copper oxide in combination with the oxide of magnesium, barium, sodium, nickel, silver, lithium, potassium, cesium, zinc, cobalt and the like or mixtures thereof. In another example, the hydrogenation catalyst can comprise cobalt metal in combination with zinc and copper oxides.

The esterification effluent may be purified prior to hydrogenation or may proceed directly to the hydrogenation reaction. The hydrogenation reaction produces a second ethylene glycol. The second ethylene glycol may or may not be further purified before separation into a product ethylene glycol and a first ethylene glycol which is recycled to the esterification step (F).

The present invention provides in a second embodiment a process for the preparation of glycolic acid, comprising
(A) feeding carbon monoxide, methylene dipropionate, propionic acid, and water to a hydrocarboxylation reactor zone comprising a solid acid catalyst to produce an effluent comprising esters of glycolic and propionic acids;
(B) hydrolyzing the effluent to produce a hydrolyzed mixture comprising glycolic acid and propionic acid;
(C) recovering the propionic acid from the hydrolyzed mixture by extracting the hydrolyzed mixture with a hydrophobic solvent selected from at least one of the group consisting of n-propyl acetate, i-propyl acetate, n-butyl acetate, i-butyl acetate, s-butyl acetate, methyl propionate, ethyl propionate, i-propyl propionate, methyl tertiary-butyl ether, methyl i-butyl ketone, methyl i-propyl ketone, methyl propyl ketone, and toluene to form an aqueous raffinate phase comprising a major amount of the glycolic acid contained in the hydrolyzed mixture and an organic extract phase comprising a major amount of the propionic acid contained in the hydrolyzed mixture; and
(D) separating the aqueous raffinate phase and the organic extract phase.

The examples of the first embodiment regarding methylene dipropionate, propionic acid, molar ratio of propionic acid to methylene dipropionate, molar ratio of water to methylene dipropionate, carbon monoxide, hydrocarboxylation reaction zone process conditions, solid acid catalysts, esters of glycolic and propionic acids, hydrolyzing and hydrolyzed mixture composition, extraction, hydrophobic solvent and hydrophilic solvent, as well as feed ratios of each solvent to the hydrolyzed mixture on a weight basis, separation of the organic extract and aqueous raffinate, separation and recycle of the propionic acid and hydrophobic solvent, esterification of the glycolic acid and hydrogenation of the glycolate ester oligomers and glycolic acid oligomers to produce ethylene glycol apply to the second embodiment.

For example, the process of the invention includes an aspect wherein the feeding of the methylene dipropionate, propionic acid, and water in step (A) occurs at a molar ratio of propionic acid:methylene dipropionate of from 0.01:1 to 6:1 or 0.01:1 to 3:1 and at a molar ratio of water:methylene dipropionate of from 0.25:1 to 2:1 or 0.5:1 to 1.5:1. In another example, the hydrolyzed mixture comprises the molar ratio water:glycolic acid of from 1:1 to 8:1 or 1:1 to 6:1 or 1:1 to 4:1. In another example the hydrophobic solvent is selected from at least one of the group consisting of n-propyl acetate, i-propyl acetate, methyl propionate, ethyl propionate, i-propyl propionate, methyl tertiary-butyl ether, and methyl i-butyl ketone.

In another example, greater than 90 weight percent of the propionic acid is recovered in the organic extract phase and greater than 90 weight percent of the glycolic acid is recovered in the aqueous raffinate phase. In another example, the extracting of step (C) occurs in a continuous counter-current extractor, wherein the aqueous raffinate phase exits the bottom of the extractor and the organic extract phase exits the top of the extractor, the hydrophobic solvent is fed to the extractor below the hydrolyzed mixture, and the feed ratio of the hydrophobic solvent to the hydrolyzed mixture ranges from 0.5:1 to 10:1 or 0.5:1 to 4:1 on a weight basis. Additionally, a hydrophilic solvent can be fed to the extractor above the hydrolyzed mixture, wherein the feed ratio of the hydrophilic solvent to the hydrolyzed mixture ranges from 0.01:1 to 5:1 on a weight basis, and the feed ratio of the hydrophobic solvent to the hydrolyzed mixture ranges from 0.5:1 to 4:1 on a weight basis.

In another example of the process of the present invention, the molar ratio of carbon monoxide to methylene dipropionate ranges from 1:1 to 10:1, and the hydrocarboxylation reaction zone is operated at a pressure of from 35 bar gauge to 200 bar gauge and a temperature of from 80° C. to 220° C.

In yet another example, the above process further comprises (E) separating the organic extract phase into the hydrophobic solvent and the propionic acid, recycling the hydrophobic solvent to step (C), and recycling the propionic acid to step (A); (F) reacting a first ethylene glycol with the aqueous raffinate phase while simultaneously removing water to produce an esterification effluent comprising glycolate ester oligomers and glycolic acid oligomers and an overhead stream comprising water; and (G) reacting hydrogen with the esterification effluent to produce a second ethylene glycol, separating the second ethylene glycol into a product ethylene glycol and the first ethylene glycol, recycling the first ethylene glycol to step (F).

FIG. 1 presents, a non-limiting embodiment of the instant invention described herein in detail. In the embodiment of the invention as laid out in FIG. 1, Carbon Monoxide Stream 1, methylene dipropionate as MDP Stream 2, Propionic Acid Stream 3, and Water Stream 13 are fed to Hydrocarboxylation Reactor 50 which comprises a fixed bed, solid catalyst (not shown). The Effluent Stream 4 comprises the esters of glycolic and propionic acid including 2-propionoxyacetic acid and (2'-propionyloxy)acetoxyacetic acid. Effluent Stream 4 and Water Stream 8 are fed to Hydrolyzer 55. Hydrolyzer 55 is operated at sufficient temperature, pressure, and residence time to produce Hydrolyzed Mixture Stream 9 comprising glycolic acid, propionic acid, and water. Hydrolyzed Mixture Stream 9 is extracted with Hydrophobic Solvent Stream 11, such as methyl tertiary-butyl ether, in Extractor 60, to produce Organic Extract Stream 10 and Aqueous Raffinate Stream 12. Organic Extract Stream 10 can be separated into Propionic Stream 3 and Hydrophobic Solvent Stream 11 in Separator 70. Separator 70 can be, for example a distillation column. Propionic Acid Stream 3 is recycled to Hydrocarboxylation Reactor 50 and Hydrophobic Solvent Stream 11 is recycled to Extractor 60.

The invention can be further illustrated by the following examples of preferred embodiments thereof, although it will be understood that these examples are included merely for purposes of illustration and are not intended to limit the scope of the invention.

EXAMPLES

The compounds and abbreviations given in Table 1 are used throughout the Examples section. Structures for each compound are also given.

TABLE 1

| Compound Names, Structures, and Abbreviation | | |
|---|---|---|
| Name | Structure | Code |
| Glycolic Acid | HO–CH₂–C(=O)–OH | G1 |
| (2-hydroxyacetoxy)-acetic acid | HO–CH₂–C(=O)–O–CH₂–C(=O)–OH | G2 |
| 2-(2'-hydroxyacetoxy)-acetoxyacetic acid | HO–CH₂–C(=O)–O–CH₂–C(=O)–O–CH₂–C(=O)–OH | G3 |
| 2-(2'-(2''-hydroxyacetoxy)-acetoxy)acetoxyacetic acid | HO–CH₂–C(=O)–O–CH₂–C(=O)–O–CH₂–C(=O)–O–CH₂–C(=O)–OH | G4 |
| Acetic Acid | CH₃–C(=O)–OH | A2 |
| Acetoxyacetic Acid | CH₃–C(=O)–O–CH₂–C(=O)–OH | A2GH |
| Propionic Acid | CH₃CH₂–C(=O)–OH | A3 |
| 2-Propionoxyacetic Acid | CH₃CH₂–C(=O)–O–CH₂–C(=O)–OH | A3GH |
| 2-Propionoxyacetic Acid Oligomer | CH₃CH₂–C(=O)–O–[CH₂–C(=O)–O]$_n$–H  n = 2–4 | A3GnH  n = 2–4 |
| Valeric Acid | CH₃CH₂CH₂CH₂–C(=O)–OH | A5 |
| Valeryloxyacetic Acid | CH₃CH₂CH₂CH₂–C(=O)–O–CH₂–C(=O)–OH | A5GH |

TABLE 1-continued

Compound Names, Structures, and Abbreviation

| Name | Structure | Code |
|---|---|---|
| (2'-Valeryloxy)-acetoxyacetic Acid | [structure] | A5G2H |
| [2'-(2''-Valeryloxy)acetoxy]-acetoxyacetic Acid | [structure] | A5G3H |
| Formaldehyde | [structure] | F0 |
| Methylene Glycol | HO–CH$_2$–OH | F1 |
| Polymethylene glycol | HO–(CH$_2$O)$_n$–H, n = 2-10 | Fn, n = 2-10 |
| Formic Acid | [structure] | A1 |
| Diglycolic Acid | [structure] | DG |
| 2-Methoxyacetic Acid | [structure] | MGH |
| Methyl Glycolate | [structure] | MG |
| Methylene Diacetate | [structure] | MDA |
| Methylene Dipropionate | [structure] | MDP |

Materials—Acetic and propionic acids (99.5%), nonafluorobutanesulfonic acid and AMBERLYST 36 ion exchange resin were purchased from Aldrich Chemical Company. AMBERLYST resin, manufactured by Rohm & Hass Chemical Company, is crosslinked polystyrene beads that have been sulfonated. AMBERLYST 36D is <1.65% wet with 5.4 meq/g acid capacity and a recommended maximum operating temperature of 150° C. Sulfuric acid was purchased from J. T. Baker, trifluoromethanesulfonic acid (also known as triflic acid) and bis(trifluoromethylsulfonyl)amide were purchased from SynQuest Labs, Inc., tetrafluoroethanesulfonic acid was purchased from DuPont Chemical Company. Paraformaldehyde (90% min) was purchased from Kodak. Solid acid catalysts were received from suppliers as detailed below. All chemicals were used as received except as noted below.

Yield—Ultimately, the hydrocarboxylation process is used to produce glycolic acid. The crude product from a hydrocarboxylation reaction, which takes place in carboxylic acid, comprises the esters of glycolic and carboxylic acids. For example, when the carboxylic acid is propionic acid, the crude product comprises methyl glycolate (MG), glycolic acid (G1) and its oligomers (Gn, n=2-5) and 2-propionoxyacetic acid (A3 GH) and its oligomers (A3GnH, n=2-4). When a GC method was used, the yield of desired products was calculated based upon the total moles of glycolic acid moiety. The term "glycolic acid moiety," as used herein, refers to the O—CH$_2$—CO$_2$ segment of a molecule, for example, the segment in glycolic acid, a glycolic acid oligomer, or an ester of glycolic and carboxylic acids. The glycolic acid moieties divided by the moles of formaldehyde fed gives the yield. When an LC method was used, all of the glycolic acid moieties are converted to glycolic acid by the sample preparation. The yield was calculated simply as the moles of glycolic acid divided by the moles of formaldehyde fed.

Selectivity—Selectivities to glycolic acid were calculated as the total moles of desired product for GC method as given above or the total moles of glycolic acid for the HPLC method divided by moles of all products formed from formaldehyde such as formic acid, methyl glycolate, diglycolic acid, and others.

Gas Chromatography (GC) Method 1. Samples were analyzed using a Hewlett-Packard HP-5890 chromatograph equipped with split injectors and FIDs. The injector and detector port temperatures were 250° C. and 300° C., respectively. A DB-5 [(5% phenyl)-methylpolysiloxane] capillary column was employed. Hydrogen was used as the carrier gas with a column head pressure of 9 psig and a column flow of 1.6 ml/minute, which gave a carrier gas linear velocity of 43 cm/second. 0.5-µl of the prepared sample solution was injected with a split ratio of 40:1. The column temperature was programmed as follows: the initial oven temperature was set at 80° C. and was held for 3 minutes, the oven was then ramped up to 280° C. at a rate of 10° C./minute and was held at 280 for 7 minutes. Samples were prepared for gas chromatographic analysis according to the following procedure: 0.1±0.001 g of sample, 200.0 µl ISTD solution (1% by volume of decane in pyridine) and 1.0 ml of BSTFA (N,O-bis (tri-methylsilyl)trifluoroacetamide) with 1% TMSCl (trimethylchlorosilane) were heated in a vial at 80° C. for 30 minutes to ensure complete derivatization. A 0.5-µl sample of this derivatized solution was injected for GC analysis.

For a typical crude reaction product, 26 species were identified using GC/MS. For the example of propionic acid as the carboxylic acid, the desired products are methyl glycolate (MG), glycolic acid (G1) and its oligomers (Gn, n=2-5) and 2-propionoxyacetic acid (A3 GH) and its oligomers (A3GnH, n=2-4). Identified co-products include formic acid (A1), and diglycolic acid (DG). Unreacted starting materials are in the form of free formaldehyde (F0), methylene glycol (F1) and polymethylene glycol (Fn, n=2-10).

Gas Chromatography (GC) Method 2. The components of samples were first reacted with BSTFA in the presence of pyridine to the corresponding TMS-derivatives including water, which were then separated and quantified by an internal standard (decane or dodecane) wt % calibrated GC method. The volume ratio of sample to derivatization reagent (BSTFA) and pyridine (containing the internal standard compound) was 0.1 g: 1 ml: 0.2 ml in a GC vial, which was heated at 80° C. for 30 minutes to ensure complete derivatization. The GC method uses a DB-1301 capillary column or equivalent (6% cyanopropylphenyl/94% dimethylpolysiloxane stationary phase, 60 meters×0.32 mm ID×1.0 um film thickness), a split injector (at 280° C.), a flame ionization detector (at 300° C.), helium carrier gas at a constant linear velocity of 27 cm/sec (a Shimadzu GC 2010 or equivalent) or at an initial column head pressure of 17 psig, an oven temperature program of 80° C. initial temp for 6 min, 4° C./min temp ramp to 150° C. held for 0 min and 10° C./min temp ramp to 290° C. for 17.5 min final hold time. 1 µl of the prepared sample solution was injected with a split ratio of 40:1 Analytes include: MeOH, A1, water, heptane, toluene, G1 and higher oligomers, A5 GH and higher oligomers, DG, methyl valerate, and MG.

High Pressure Liquid Chromatography (HPLC) Method 1. Samples were prepared by pipetting 100 µl of sample into a 10 mL volumetric flask, adding a few mLs of water, ten drops of conc. $H_3PO_4$, and diluting to the mark with water. An aliquot of sample was injected onto an Agilent 1100 HPLC instrument for analysis using a BIORAD Fast Acid Analysis Column (100×7.8 mm) at 60° C. The sample is eluted using 10 mM sulfuric acid in water with a flow rate of 1 mL/min. Glycolic acid was detected at 210 nm on the UV detector. An external standard was used for calibration along with a dilution factor in a sequence table. The results are reported as ppm using a two-level calibration curve (100 and 1000 ppm) for each acid.

High Pressure Liquid Chromatography (HPLC) Method 2. Glycolic acid concentration was quantitatively determined by an Agilent 1100 HPLC using a Hamilton PRP-X300 exclusion column (250×4.1 mm). Glycolic acid was detected at 210 nm on the UV detector. Two eluents were used, where eluent A is 5 mM $H_3PO_4$ in 1% acetonitrile/99% water and eluent B is 5 mM $H_3PO_4$ in 10% acetonitrile/90% water. The following gradient was used: 100% A for 2 min; →100% B 5 min; Hold for 3 mins; →100% A 0.1 mins; equilibrate 4.9 mins for a total run time of 15 minutes. HPLC samples were prepared according to the following method. The samples of crude hydrocarboxylation reaction are hydrolyzed and diluted for analysis according to the following procedure: 200 mg of sample is weighed into a 10 mL volumetric flask, then 0.5 mL of 40% NaOH is added. After 10 minutes, 2 mL of water is added and the solution is allowed to sit for another 10 minutes. The solution is then diluted to the mark with water. A milliliter of this solution is then diluted tenfold before analysis.

High Pressure Liquid Chromatography (HPLC) Method 3. Samples were analyzed by liquid chromatography for glycolic acid using ion-exclusion chromatography after samples were subjected to acid hydrolysis in aqueous 25% v/v $H_2SO_4$ at 80° C. for 30 minutes. The analytes were separated on a Hamilton PRP X300 column using a 10 mM $H_3PO_4$ mobile phase with a 1-20% v/v acetonitrile gradient. The eluting components were monitored using a UV detector set at 210 nm and their concentrations calculated based on calibration using external standards. Formaldehyde was determined by liquid chromatographic separation of the 2,4-dinitrophenylhydrazone derivative of formaldehyde and its subsequent detection by UV at 360 nm. The same acid hydrolysate from the procedure above was reacted with dinitrophenylhydrazine, then analyzed using a Phenomenex Luna C8 column using a 1:1 water:acetonitrile mobile phase under isocratic conditions. The formaldehyde concentration was calculated based on calibration using external standards.

X-ray method for triflic acid. Reactor effluent and extraction samples were analyzed for sulfur using a wavelength dispersive x-ray fluorescence (WDXRF) semi-quantitative application called UNIQUANT™ (UQ). UQ affords standardless XRF analysis of samples. The data were mathematically corrected for matrix differences between calibration standards and samples as well as absorption and enhancement effects; i.e., inter-element effects. Instrument conditions for sulfur analysis were: Line, $K_a$; kV, 40; mA, 60; Filter, none; Collimator Spacing (mm), 150; Crystal, Ge III-C; Peak Angle (2q), 110.6712; Detector, flow; PHD Lower, 35; PHD Upper, 70; Collimator Mask (mm), 30; Peak time (s), 30. Sulfur weight fraction numbers were converted to triflic acid weight equivalents by the factor 4.68 (ratio of molecular weight of triflic acid to that of sulfur).

Example 1

20% W-heteropoly/silica catalyst purchased from Johnson Matthey was used as received. A 50 mL Hastelloy 276C autoclave was heated with a heating block, with temperature control provided by feedback via a thermocouple in the autoclave thermowell. Pure carbon monoxide gas (>99.9%) was fed to the autoclave via a high pressure regulator. The autoclave was charged with the paraformaldehyde (3.12 g, 0.099 mol), propionic acid (30.74 g, 0.41 mol), 20% W-heteropoly/silica catalyst (1.9 g), assembled, and pressurized with 200 psig of nitrogen and vented. This purging procedure was repeated two times. To remove nitrogen from the autoclaves, they were purged with 200 psig of carbon monoxide. Then the reactors were pressurized with 200 psig of carbon monoxide and heated with stirring to 140° C. The reactor was then pressurized to 1000 psig carbon monoxide and the pressure was maintained from the surge tank. After a 2 hour hold time, the reactor was cooled to room temperature and vented. Finally the autoclave was purged with nitrogen and unloaded. The reaction content was analyzed by GC and/or HPLC. Table 2 gives the yield.

Examples 2-7

Example 1 was repeated using the catalyst and catalyst loading and hold time given in Table 2. The resulting yields are also given in Table 2.

For Examples 4 and 5, the AMBERLYST catalyst preparation was as follows. The resin was washed up-flow with six bed volumes of ambient temperature distilled water over a period of 15 minutes. The washed resins were then dried in a vacuum oven at 109° C. and placed in a desiccator until needed.

For Examples 6 and 7 the SMOPEX 101 catalyst preparation was as follows. To 20 g of SMOPEX catalyst, in 250 mL beaker, 50 mL of propionic acid was added. The catalyst was allowed to sit for 15 min and then filtered using vacuum filtration. The vacuum was turned off and 20 mL of propionic acid was passed through the catalyst. This step was repeated three times to ensure that all of the water was washed off of the catalyst. Finally the solid was dried under house vacuum overnight.

TABLE 2

Hydrocarboxylation of Paraformaldehyde in Propionic Acid Catalyzed by Strongly Acidic Solid Acid Catalysts.

| EX | catalyst | loading (wt %) | temp (° C.) | time (h) | yield (%) |
|----|----------|----------------|-------------|----------|-----------|
| 1 | 20% W-heteropoly/silica | 5.1 | 140 | 2 | 2.1 |
| 2 | $SiO_2/Al_2O_3$ | 5 | 140 | 2 | 2.6 |
| 3 | SAC-13 | 15 | 140 | 3 | 82.3 |
| 4 | AMBERLYST 36 (5.4 mmol/g) | 5.0 | 140 | 2 | 71.1 |
| 5 | AMBERLYST 36 (5.4 mmol/g) | 5.0 | 140 | 3 | 75.7 |
| 6 | SMOPEX 101 (4% crosslinked) | 5.0 | 140 | 3 | 61.4 |
| 7 | SMOPEX 101 (12% crosslinked) | 5.0 | 140 | 3 | 69.4 |

The following examples demonstrate the effect of pressure, temperature, and water content on the batch hydrocarboxylation of paraformaldehyde in propionic acid using a dry AMBERLYST 36 solid acid catalyst.

Example 8

A 300 ml Hastelloy 276C autoclave was charged with paraformaldehyde (15.99 g, 0.53 mol), dry AMBERLYST 36 catalyst (9.3 g), propionic acid (157.9 g, 2.13 mol), and formic acid (3.8 g). The autoclave was then assembled and pressurized with 200 psig of $N_2$ and vented. This purging procedure was repeated two times. The autoclave was purged with 200 psig carbon monoxide in order to remove $N_2$. The reactor was pressurized with carbon monoxide to 500 psig and heated with stirring to 100° C. Once the desired temperature was reached, the reactor was pressurized to 1500 psig carbon monoxide and the pressure of the autoclave was maintained from a surge tank. Samples of the reaction were taken over the duration of the experiment at approximately 0.5, 1, 1.5, 2, 2.5, and 3 hours. When the reaction time was complete, the reactor was cooled to room temperature and vented. The autoclave was purged with nitrogen and the product mixture removed. The samples were analyzed by GC. The temperature and pressure; the weight percent paraformaldehyde, propionic acid, and water; and the yield of desired products and selectivity are given in Table 3. The concentration of formic acid ranged from 2.2 weight percent to 2.4 weight percent.

Examples 9-32

Example 8 was repeated for examples 9-32 with no water, as in Example 8, or water (nominally 4.58 g, 0.5 eq.), or water (nominally 9.12 g, 1.0 eq.) with formic acid added at an amount of 2.0 wt % of the charged composition. The feed composition as well as the temperature and pressure of the reactor are as noted in Table 3. The temperature and pressure; the weight percent paraformaldehyde, propionic acid, and water; and the yield of desired products and selectivity are given in Table 3.

TABLE 3

Hydrocarboxylation of Paraformaldehyde in Propionic Acid Catalyzed by AMBERLYST 36D (4.6-4.8 wt %).

| EX | Pressure (psig) | Temperature (° C.) | Feed (wt %) | | | Time (h) | Yield of desired products (%) | Selectivity (%) |
|----|-----------------|--------------------|-|-|-|----------|-------------------------------|-----------------|
| | | | F0 | A3 | Water | | | |
| 8 | 1,500 | 100 | 9.0 | 88.8 | 0.0 | 0.5 | 14 | 53 |
| | | | | | | 1.0 | 29 | 68 |
| | | | | | | 1.5 | 43 | 73 |
| | | | | | | 2.0 | 53 | 79 |
| | | | | | | 2.5 | 64 | 85 |
| | | | | | | 3.0 | 71 | 88 |
| 9 | 1,000 | 100 | 9.0 | 88.8 | 0.0 | 0.5 | 25 | 63 |
| | | | | | | 1.0 | 42 | 72 |
| | | | | | | 1.5 | 62 | 83 |
| | | | | | | 2.0 | 73 | 99 |

TABLE 3-continued

Hydrocarboxylation of Paraformaldehyde in Propionic Acid Catalyzed by AMBERLYST 36D (4.6-4.8 wt %).

| EX | Pressure (psig) | Temperature (° C.) | Feed (wt %) F0 | A3 | Water | Time (h) | Yield of desired products (%) | Selectivity (%) |
|---|---|---|---|---|---|---|---|---|
|  |  |  |  |  |  | 2.5 | 81 | 100 |
|  |  |  |  |  |  | 3.0 | 86 | 101 |
| 10 | 500 | 100 | 9.0 | 88.8 | 0.0 | 0.5 | 11 | 100 |
|  |  |  |  |  |  | 1.0 | 20 | 99 |
|  |  |  |  |  |  | 1.5 | 27 | 95 |
|  |  |  |  |  |  | 2.0 | 36 | 88 |
|  |  |  |  |  |  | 2.5 | 45 | 84 |
|  |  |  |  |  |  | 3.0 | 53 | 81 |
| 11 | 1,500 | 100 | 8.6 | 84.4 | 4.9 | 0.5 | 2 | 79 |
|  |  |  |  |  |  | 1.0 | 2 | 81 |
|  |  |  |  |  |  | 1.5 | 3 | 83 |
|  |  |  |  |  |  | 2.0 | 10 | 80 |
|  |  |  |  |  |  | 2.5 | 11 | 82 |
|  |  |  |  |  |  | 3.0 | 12 | 89 |
| 12 | 1,000 | 100 | 8.5 | 84.4 | 4.9 | 0.5 | 7 | 84 |
|  |  |  |  |  |  | 1.0 | 7 | 69 |
|  |  |  |  |  |  | 1.5 | 8 | 69 |
|  |  |  |  |  |  | 2.0 | 9 | 68 |
|  |  |  |  |  |  | 2.5 | 10 | 65 |
|  |  |  |  |  |  | 3.0 | 12 | 66 |
| 13 | 500 | 100 | 8.6 | 84.4 | 4.9 | 0.5 | 5 | 83 |
|  |  |  |  |  |  | 1.0 | 5 | 82 |
|  |  |  |  |  |  | 1.5 | 6 | 91 |
|  |  |  |  |  |  | 2.0 | 1 | 80 |
|  |  |  |  |  |  | 2.5 | 7 | 85 |
|  |  |  |  |  |  | 3.0 | 8 | 71 |
| 14 | 750 | 100 | 8.6 | 84.4 | 4.9 | 0.5 | 5 | 78 |
|  |  |  |  |  |  | 1.0 | 6 | 75 |
|  |  |  |  |  |  | 1.5 | 7 | 73 |
|  |  |  |  |  |  | 2.0 | 7 | 70 |
|  |  |  |  |  |  | 2.5 | 8 | 70 |
|  |  |  |  |  |  | 3.0 | 9 | 66 |
| 15 | 750 | 100 | 9.0 | 88.8 | 0.0 | 0.5 | 12 | 95 |
|  |  |  |  |  |  | 1.0 | 24 | 92 |
|  |  |  |  |  |  | 1.5 | 28 | 96 |
|  |  |  |  |  |  | 2.0 | 37 | 81 |
|  |  |  |  |  |  | 2.5 | 46 | 87 |
|  |  |  |  |  |  | 3.0 | 54 | 85 |
| 16 | 500 | 100 | 8.8 | 86.6 | 2.5 | 0.5 | 7 | 99 |
|  |  |  |  |  |  | 1.0 | 8 | 93 |
|  |  |  |  |  |  | 1.5 | 9 | 90 |
|  |  |  |  |  |  | 2.0 | 10 | 86 |
|  |  |  |  |  |  | 2.5 | 13 | 85 |
|  |  |  |  |  |  | 3.0 | 15 | 82 |
| 17 | 750 | 100 | 8.8 | 86.6 | 2.5 | 0.5 | 8 | 89 |
|  |  |  |  |  |  | 1.0 | 10 | 96 |
|  |  |  |  |  |  | 1.5 | 13 | 87 |
|  |  |  |  |  |  | 2.0 | 16 | 91 |
|  |  |  |  |  |  | 2.5 | 19 | 83 |
|  |  |  |  |  |  | 3.0 | 23 | 91 |
| 18 | 1000 | 100 | 8.8 | 86.6 | 2.5 | 0.5 | 6 | 102 |
|  |  |  |  |  |  | 1.0 | 7 | 113 |
|  |  |  |  |  |  | 1.5 | 7 | 108 |
|  |  |  |  |  |  | 2.0 | 7 | 104 |
|  |  |  |  |  |  | 2.5 | 9 | 101 |
|  |  |  |  |  |  | 3.0 | 12 | 82 |
| 19 | 1,500 | 100 | 8.8 | 86.6 | 2.5 | 0.5 | 10 | 80 |
|  |  |  |  |  |  | 1.0 | 13 | 79 |
|  |  |  |  |  |  | 1.5 | 17 | 79 |
|  |  |  |  |  |  | 2.0 | 20 | 80 |
|  |  |  |  |  |  | 2.5 | 24 | 80 |
|  |  |  |  |  |  | 3.0 | 28 | 80 |
| 20 | 1,500 | 100 | 9.0 | 88.8 | 0.0 | 0.5 | 17 | 94 |
|  |  |  |  |  |  | 1.0 | 31 | 81 |
|  |  |  |  |  |  | 1.5 | 44 | 82 |
|  |  |  |  |  |  | 2.0 | 58 | 89 |
|  |  |  |  |  |  | 2.5 | 68 | 90 |
|  |  |  |  |  |  | 3.0 | 75 | 92 |
| 21 | 500 | 100 | 9.0 | 88.8 | 0.0 | 0.5 | 9 | 73 |
|  |  |  |  |  |  | 1.0 | 12 | 87 |
|  |  |  |  |  |  | 1.5 | 17 | 85 |
|  |  |  |  |  |  | 2.0 | 21 | 81 |

TABLE 3-continued

Hydrocarboxylation of Paraformaldehyde in Propionic Acid Catalyzed by AMBERLYST 36D (4.6-4.8 wt %).

| EX | Pressure (psig) | Temperature (° C.) | Feed (wt %) F0 | A3 | Water | Time (h) | Yield of desired products (%) | Selectivity (%) |
|---|---|---|---|---|---|---|---|---|
|  |  |  |  |  |  | 2.5 | 24 | 81 |
|  |  |  |  |  |  | 3.0 | 28 | 81 |
| 22 | 1,500 | 100 | 8.6 | 84.4 | 4.9 | 0.5 | 4 | 27 |
|  |  |  |  |  |  | 1.0 | 4 | 28 |
|  |  |  |  |  |  | 1.5 | 5 | 28 |
|  |  |  |  |  |  | 2.0 | 6 | 24 |
|  |  |  |  |  |  | 2.5 | 6 | 24 |
|  |  |  |  |  |  | 3.0 | 7 | 26 |
| 23 | 500 | 100 | 8.5 | 84.4 | 4.9 | 0.5 | 1 | 77 |
|  |  |  |  |  |  | 1.0 | 6 | 87 |
|  |  |  |  |  |  | 1.5 | 6 | 80 |
|  |  |  |  |  |  | 2.0 | 6 | 80 |
|  |  |  |  |  |  | 2.5 | 7 | 75 |
|  |  |  |  |  |  | 3.0 | 8 | 76 |
| 24 | 1000 | 100 | 8.8 | 86.6 | 2.5 | 0.5 | 6 | 77 |
|  |  |  |  |  |  | 1.0 | 10 | 82 |
|  |  |  |  |  |  | 1.5 | 12 | 90 |
|  |  |  |  |  |  | 2.0 | 13 | 87 |
|  |  |  |  |  |  | 2.5 | 19 | 90 |
|  |  |  |  |  |  | 3.0 | 21 | 90 |
| 25 | 500 | 140 | 9.0 | 88.8 | 0.0 | 0.5 | 45 | 81 |
|  |  |  |  |  |  | 1.0 | 63 | 85 |
|  |  |  |  |  |  | 1.5 | 77 | 99 |
|  |  |  |  |  |  | 2.0 | 78 | 104 |
|  |  |  |  |  |  | 2.5 | 78 | 106 |
|  |  |  |  |  |  | 3.0 | 79 | 108 |
| 26 | 1,500 | 140 | 8.6 | 84.4 | 4.9 | 0.5 | 38 | 75 |
|  |  |  |  |  |  | 1.0 | 48 | 78 |
|  |  |  |  |  |  | 1.5 | 59 | 83 |
|  |  |  |  |  |  | 2.0 | 65 | 90 |
|  |  |  |  |  |  | 2.5 | 68 | 92 |
|  |  |  |  |  |  | 3.0 | 69 | 92 |
| 27 | 1,000 | 120 | 8.6 | 86.6 | 2.5 | 0.5 | 16 | 68 |
|  |  |  |  |  |  | 1.0 | 24 | 70 |
|  |  |  |  |  |  | 1.5 | 32 | 70 |
|  |  |  |  |  |  | 2.0 | 39 | 86 |
|  |  |  |  |  |  | 2.5 | 48 | 87 |
|  |  |  |  |  |  | 3.0 | 52 | 89 |
| 28 | 500 | 140 | 8.6 | 84.4 | 4.9 | 0.5 | 20 | 63 |
|  |  |  |  |  |  | 1.0 | 32 | 65 |
|  |  |  |  |  |  | 1.5 | 40 | 69 |
|  |  |  |  |  |  | 2.0 | 54 | 76 |
|  |  |  |  |  |  | 2.5 | 48 | 79 |
|  |  |  |  |  |  | 3.0 | 52 | 82 |
| 29 | 1,500 | 140 | 9.0 | 88.8 | 0.0 | 0.5 | 67 | 97 |
|  |  |  |  |  |  | 1.0 | 82 | 100 |
|  |  |  |  |  |  | 1.5 | 75 | 102 |
|  |  |  |  |  |  | 2.0 | 84 | 107 |
|  |  |  |  |  |  | 2.5 | 84 | 108 |
|  |  |  |  |  |  | 3.0 | 84 | 108 |
| 30 | 2,000 | 140 | 9.0 | 88.9 | 0.0 | 0.5 | 78 | 97 |
|  |  |  |  |  |  | 1.0 | 83 | 100 |
|  |  |  |  |  |  | 1.5 | 84 | 102 |
|  |  |  |  |  |  | 2.0 | 85 | 103 |
|  |  |  |  |  |  | 2.5 | 86 | 104 |
|  |  |  |  |  |  | 3.0 | 87 | 104 |
| 31 | 2,000 | 140 | 8.6 | 84.5 | 4.9 | 0.5 | 38 | 77 |
|  |  |  |  |  |  | 1.0 | 61 | 84 |
|  |  |  |  |  |  | 1.5 | 71 | 87 |
|  |  |  |  |  |  | 2.0 | 76 | 89 |
|  |  |  |  |  |  | 2.5 | 77 | 90 |
|  |  |  |  |  |  | 3.0 | 79 | 91 |
| 32 | 2,000 | 140 | 8.8 | 86.6 | 2.5 | 0.5 | 60 | 86 |
|  |  |  |  |  |  | 1.0 | 72 | 91 |
|  |  |  |  |  |  | 1.5 | 78 | 93 |
|  |  |  |  |  |  | 2.0 | 80 | 94 |
|  |  |  |  |  |  | 2.5 | 79 | 95 |
|  |  |  |  |  |  | 3.0 | 80 | 95 |

The following examples demonstrate the hydrocarboxylation of paraformaldehyde using a triflic acid catalyst in acetic, propionic, n-butyric, i-butyric, valeric, and hexanoic acids.

Example 33

A 100 mL zirconium high pressure autoclave was fitted with an impeller, gas inlet tube, sample tube, and thermowell. The autoclave was heated with a heating block, with temperature control provided by feedback via a thermocouple in the autoclave thermowell. Pure carbon monoxide gas (>99.9%) was fed to the autoclave via a high pressure regulator. Triflic acid (0.562 g, 3.7 mmol), acetic acid (30.03 g, 0.5 mol) and paraformaldehyde (3.94 g, 0.125 mol) were added to the autoclave and sealed. The autoclave was secured to the stand and the system was purged with carbon monoxide and pressurized to 250 psig carbon monoxide. The temperature in the autoclave was increased to 140° C. while stirring at 1000 rpm. Upon reaching 140° C., the pressure in the autoclave was increased to 1,000 psig carbon monoxide. Once temperature and pressure were reached, a sample was taken, "time 0." The pressure and temperature were maintained for 4 hours. Subsequent samples of the reaction were taken at approximately 15, 30, 45, 60, 90, 120, 180 and 240 minutes and analyzed by HPLC. Results are given in Table 4, in terms of yield of glycolic acid and selectivity.

Example 34

Example 33 was repeated except that propionic acid (37.04 g, 0.5 mol) was charged to the autoclave in place of acetic acid. Results are given in Table 4.

Example 35

Example 33 was repeated except that n-butyric acid (44.06 g, 0.5 mol) was charged to the autoclave in place of acetic acid. Results are given in Table 4.

Example 36

Example 33 was repeated except that i-butyric acid (44.06 g, 0.5 mol) was charged to the autoclave in place of acetic acid. Results are given in Table 4.

Example 37

Example 33 was repeated except that valeric acid (51.07 g, 0.5 mol) was charged to the autoclave in place of acetic acid. Results are given in Table 4.

Example 38

Example 33 was repeated except that hexanoic acid (58.08 g, 0.5 mol) was charged to the autoclave in place of acetic acid. Results are given in Table 4.

TABLE 4

Hydrocarboxylation of Paraformaldehyde in Carboxylic Acids Catalyzed by Triflic Acid.

| EX | Carboxylic Acid | Time (h) | Yield (%) | Selectivity (%) |
|---|---|---|---|---|
| 33 | Acetic Acid | 0 | 14.1 | 79.2 |
| | | 0.3 | 45.9 | 92.0 |
| | | 0.5 | 84.1 | 93.5 |
| | | 0.8 | 92.8 | 96.5 |
| | | 1.0 | 97.2 | 95.8 |
| | | 1.3 | 96.5 | 95.8 |
| | | 1.8 | 98.9 | 97.1 |
| | | 3.0 | 98.3 | 99.4 |
| | | 4.0 | 99.9 | 98.2 |
| 34 | Propionic Acid | 0 | 7.5 | 45.1 |
| | | 0.3 | 28.1 | 74.6 |
| | | 0.5 | 59.9 | 87.1 |
| | | 0.8 | 74.1 | 89.7 |
| | | 1.0 | 76.4 | 90.6 |
| | | 1.5 | 81.9 | 92.4 |
| | | 2.4 | 85.9 | 94.0 |
| | | 2.8 | 84.9 | 94.8 |
| | | 4.0 | 83.4 | 94.2 |
| 35 | n-butyric acid | 0 | 10.2 | 74.9 |
| | | 0.3 | 40.8 | 87.1 |
| | | 0.5 | 70.0 | 94.2 |
| | | 0.8 | 90.8 | 97.5 |
| | | 1.0 | 89.9 | 97.2 |
| | | 1.3 | 97.3 | 97.9 |
| | | 1.8 | 101.1 | 97.6 |
| | | 3.0 | 104.4 | 98.3 |
| | | 4.0 | 104.1 | 98.2 |
| 36 | i-butyric | 0 | 9.8 | 67.6 |
| | | 0.3 | 21.7 | 78.8 |
| | | 0.5 | 40.1 | 82.6 |
| | | 0.8 | 46.9 | 84.7 |
| | | 1.0 | 52.7 | 86.8 |
| | | 1.5 | 57.8 | 88.5 |
| | | 2.4 | 67.0 | 92.5 |
| | | 2.8 | 66.8 | 92.3 |
| | | 4.0 | 65.6 | 93.3 |
| 37 | Valeric Acid | 0 | 9.5 | 64.5 |
| | | 0.3 | 28.4 | 72.6 |
| | | 0.5 | 55.0 | 87.2 |
| | | 0.8 | 69.1 | 92.2 |
| | | 1.0 | 82.9 | 100.0 |
| | | 1.3 | 94.4 | 99.5 |
| | | 1.8 | 96.0 | 100.0 |
| | | 3.0 | 99.3 | 98.5 |
| | | 4.0 | 100.8 | 100.0 |
| 38 | Hexanoic Acid | 0 | 7.9 | 42.2 |
| | | 0.3 | 20.9 | 55.0 |
| | | 0.5 | 41.7 | 71.4 |
| | | 0.8 | 54.5 | 77.5 |
| | | 1.0 | 65.0 | 83.3 |
| | | 1.3 | 73.9 | 87.9 |
| | | 1.8 | 77.9 | 92.9 |
| | | 3.0 | 81.8 | 94.2 |
| | | 4.0 | 84.5 | 97.2 |

For all extraction examples the partition coefficient for component A is defined as follows:

$$P(A) = \frac{\text{Weight Percent } A \text{ in Hydrophobic phase}}{\text{Weight Percent } A \text{ in Hydrophilic phase}}$$

Extraction selectivity between components A and B is defined as:

$$S(AB) = P(A)/P(B)$$

Example 39

A first standard aqueous acetic-glycolic acid solution was prepared by mixing glycolic acid, water, and acetic acid. Fifteen grams of this first standard solution was added to a separate glass vial along with fifteen grams of each of the nonpolar solvents listed in Table 5. A second standard aqueous propionic-glycolic acid solution was prepared and fifteen grams of this second standard solution was added to a separate glass vial along with fifteen grams of each of the non polar solvents listed in Table 5. The contents of each vial were mixed vigorously and allowed to settle and separate into two clear phases. All experiments were conducted at room temperature. The phases were analyzed by GC to determine acetic acid, propionic acid, and glycolic acid compositions. These analytical results were used to calculate partition coefficients and extraction selectivities. Results are summarized in Table 5. The partition coefficients and selectivities for propionic acid are higher than the corresponding values for acetic acid, thus illustrating the value of using propionic acid instead of acetic acid as a hydrocarboxylation solvent/reactant.

TABLE 5

Extraction Compositions, Partition Coefficients and Selectivities for Mixtures Containing Acetic Acid and Propionic acid.

| Ex. | Solvent | acid | acid (g) | glycolic (g) | water (g) | solv. (g) | P (acid) | P (glycolic) | S (acid/glycolic) |
|---|---|---|---|---|---|---|---|---|---|
| 39a | Toluene | acetic | 3.6 | 2.4 | 9 | 15 | 0.08 | <0.001 | >80 |
| 39b | Heptane | acetic | 3.6 | 2.4 | 9 | 15 | 0.02 | <0.001 | >20 |
| 39c | methyl propionate | acetic | 3.6 | 2.4 | 9 | 15 | 0.80 | 0.14 | 6 |
| 39d | MTBE | acetic | 3.6 | 2.4 | 9 | 15 | 1.00 | 0.07 | 14 |
| 39e | Toluene | propionic | 3.6 | 2.4 | 9 | 15 | 0.70 | <0.001 | >70 |
| 39f | Heptane | propionic | 3.6 | 2.4 | 9 | 15 | 0.10 | <0.011 | >10 |
| 39g | methyl propionate | propionic | 3.6 | 2.4 | 9 | 15 | 2.50 | 0.16 | 16 |
| 39h | MTBE | propionic | 3.6 | 2.4 | 9 | 15 | 3.40 | 0.09 | 38 |

Examples 40-50

These examples illustrate the selective extractive separation of n-valeric, n-butyric (nHOBu), iso-butyric (iHOBu), and propionic (HOPr) acids from highly concentrated aqueous glycolic acid. Aqueous glycolic acid-water-carboxylic acid mixtures were prepared and added to separate glass vials along with the amount of each hydrophobic solvent as listed in Table 6. The contents of each vial were mixed vigorously and allowed to settle and separate into two clear phases. All experiments were conducted at room temperature. The phases were analyzed by GC to determine carboxylic acid and glycolic acid compositions. These analytical results were used to calculate partition coefficients and selectivities. Results are summarized in Table 6.

TABLE 6

Extraction compositions, Partition Coefficients and Selectivities.

| Ex. | Solvent | acid | acid (g) | glycolic (g) | water (g) | solv. (g) | P (acid) | P (glycolic) | S (acid/glycolic) |
|---|---|---|---|---|---|---|---|---|---|
| 40 | Toluene | n-butyric | 10 | 8 | 2 | 10 | 5.2 | 0.035 | 148.8 |
| 41 | MTBE | n-butyric | 10 | 8 | 12 | 15 | 7.4 | 0.189 | 39.4 |
| 42 | Heptane | n-butyric | 10 | 8 | 2 | 10 | 3.4 | 0.015 | 220.4 |
| 43 | Toluene | i-butyric | 10 | 8 | 2 | 10 | 7.4 | 0.027 | 271.6 |
| 44 | MTBE | i-butyric | 10 | 8 | 11 | 15 | 8.3 | 0.176 | 46.9 |
| 45 | Heptane | i-butyric | 10 | 8 | 2 | 10 | 6.7 | 0.011 | 626.6 |
| 46 | Toluene | propionic | 10 | 8 | 2 | 10 | 1.9 | 0.056 | 34.5 |
| 47 | MTBE | propionic | 10 | 8 | 12 | 15 | 2.2 | 0.341 | 6.6 |
| 48 | MIBK | propionic | 10 | 8 | 12 | 15 | 2.0 | 0.303 | 6.6 |
| 49 | heptane | n-valeric | 8 | 6 | 2 | 4 | 8.2 | 0.0001 | 5,672.1 |
| 50 | toluene | n-valeric | 8 | 6 | 2 | 4 | 13.5 | 0.030 | 446.6 |

Examples 51-58

These examples illustrate the effect of glycolic acid content on the extractive separation of n-valeric acid from glycolic acid. Aqueous glycolic acid-water-n-valeric acid mixtures were prepared and added to separate glass vials along with the amount of toluene or heptane as listed in Table 7. The contents of each vial were mixed vigorously and allowed to settle and separate into two clear phases. All experiments were conducted at room temperature. The phases were analyzed by GC to determine n-valeric acid and glycolic acid compositions. These analytical results were used to calculate partition coefficients and selectivities as shown in Table 7.

TABLE 7

Extraction Compositions, Partition Coefficients and Selectivities.

| Ex. | solvent | wt. % glycolic | acid (g) | glycolic (g) | water (g) | solv. (g) | P (acid) | P (glycolic) | S (acid/glycolic) |
|---|---|---|---|---|---|---|---|---|---|
| 51 | toluene | 75 | 8 | 5.99 | 2.00 | 4.00 | 329 | 0.44 | 748.2 |
| 52 | toluene | 50 | 8.00 | 4.01 | 4.01 | 4.02 | 636 | 0.31 | 2,041.3 |
| 53 | toluene | 25 | 7.98 | 2.01 | 6.02 | 3.99 | 763 | 0.18 | 4,183.8 |
| 54 | toluene | 0 | 7.97 | 0.00 | 8.15 | 4.03 | 1,319 | NA | NA |
| 55 | heptane | 75 | 8.09 | 6.06 | 2.02 | 4.04 | 8.0 | 0.006 | 1,419.3 |
| 56 | heptane | 50 | 8.02 | 4.05 | 4.05 | 4.01 | 12.4 | 0.006 | 2,099.0 |
| 57 | heptane | 25 | 8.11 | 2.01 | 6.04 | 4.04 | 15.0 | 0.004 | 3,767.9 |
| 58 | heptane | 0 | 8.03 | 0.00 | 8.02 | 4.19 | 18.9 | NA | NA |

Examples 59-62

These examples illustrate the effect of glycolic acid content on the extractive separation of valeric acid from triflic acid and glycolic acid. Aqueous glycolic acid-water-triflic acid mixtures were prepared and added to separate glass vials along with the amount of toluene and valeric acid as listed in Table 8. The contents of each vial were mixed vigorously and allowed to settle and separate into two clear phases. All experiments were conducted at a temperature of 50° C. The phases were analyzed by GC and X-ray to determine valeric, triflic acid, and glycolic compositions. These analytical results were used to calculate partition coefficients and selectivities as shown in Table 8.

TABLE 8

Extraction Compositions, Partition Coefficients and Selectivities of Valeric Acid, Triflic Acid and Glycolic Acid in Toluene.

| Ex. | Acid (g) | glycolic (g) | water (g) | solv. (g) | triflic (g) | P (acid) | P (glycolic) | P (triflic) | S (acid/glycolic) | S (acid/triflic) |
|---|---|---|---|---|---|---|---|---|---|---|
| 59 | 1.07 | 0.00 | 9.72 | 9.00 | 0.30 | 13.7 | NA | 0.0002 | NA | 57,499 |
| 60 | 4.00 | 0.00 | 7.77 | 7.99 | 0.24 | 38.0 | NA | 0.001 | NA | 38,376 |
| 61 | 1.02 | 7.79 | 1.95 | 9.02 | 0.30 | 2.0 | 0.001 | 0.0001 | 1,388.1 | 20,302 |
| 62 | 4.03 | 6.23 | 1.56 | 8.03 | 0.24 | 4.2 | 0.031 | 0.0012 | 136.6 | 3,414 |

Example 63

A solution rich in esters of glycolic and valeric acids was prepared by mixing 1.45 moles of valeric acid per mole of glycolic acid. This mixture was heated to reflux under vacuum to remove approximately 0.2 grams of water per gram of glycolic acid fed, to give an average degree of oligomerization of 0.84 ester bonds per mole of glycolic acid (i.e., mostly A5 GH). This source of A5 GH was used in Examples 63 and 64.

A feed was produced by mixing the source of A5 GH above with triflic acid and heptane to give the feed composition listed in Table 9. This example illustrates a simulated continuous extraction of a feed containing esters of glycolic and valeric acids, triflic acid, and heptane with a hydrophilic solvent containing 20% aqueous glycolic acid for separation of Triflic acid from A5 GH. The feed mixture was subjected to a cascaded series of twenty-four cross-flow batch extractions to simulate a six-stage continuous counter-current extraction process, with the feed mixture (20.0 g) introduced on stage six (from the top) and the aqueous glycolic acid solvent (8.0 g) on stage one (top of extractor). The multi-cycle, cascaded pattern of 24 extractions in which one feed mixture charge is added into the first cycle of the cascade, and multiple hydrophilic solvent charges are introduced into each cycle of the cascade, and with raffinate and extract compositions introduced to the next cycle of the cascade, results in a set of conditions on the final cycle which have been shown to closely approach the equilibrium composition profile of a continuous, staged, counter-current fractional extractor. For this work, three cycles were found to be sufficient to asymptotically approach continuous extraction equilibrium conditions. The simulated counter-current extraction technique used herein is well-known to those skilled in the art and is laid out in detail in Treybal ("Liquid Extraction," 2nd Ed., McGraw-Hill Book Company, New York, N.Y., 1963, pp. 349-366). The feed contained 10 weight percent hydrophobic solvent. The hydrophilic solvent (aqueous glycolic acid) to feed (including the heptane) weight ratio was 0.4:1.0. The experiment was conducted at room temperature. The final simulated raffinate (19.24 g—top product) and extract (8.58 g—bottom product) streams were subjected to GC and X-ray analysis to determine the compositions of the products. Results are given in Table 9 with all percentages representing weight percent. The percent recovery to the extract is based on the amount of each component in all inputs to the extractor. The percent accountability of each component is equal to total out/total in as a percentage.

TABLE 9

Simulated Extraction Results

| | Aq G1 Solvent (%) | Feed (%) | Extract (%) | Raffinate (%) | % Account | Recovery to Extract (%) |
|---|---|---|---|---|---|---|
| Water | 80.0 | 2.1 | 59.9 | 7.4 | 97 | 78.2 |
| Heptane | 0.0 | 10.0 | 0.3 | 10.1 | 99 | 1.2 |
| A5 | 0.0 | 46.5 | 13.1 | 45.1 | 106 | 11.4 |
| G1 | 20.0 | 3.5 | 14.1 | 5.6 | 100 | 52.4 |
| A5GH | 0.0 | 29.0 | 5.6 | 27.1 | 99 | 8.4 |
| G2 | 0.0 | 1.1 | 1.0 | 0.1 | 48 | 86.5 |
| A5G2H | 0.0 | 4.2 | 0.2 | 3.5 | 81 | 2.6 |
| Triflic | 0.0 | 2.0 | 4.6 | 0.0 | 100 | 99.2 |
| Other | 0.0 | 1.7 | 1.2 | 1.2 | 90 | 32.3 |

Example 64

Example 63 was repeated using a feed produced by mixing the source of A5 GH above with triflic acid to give the feed composition listed in Table 10 with the feed (20.0 g) introduced on stage three (from the top), the hydrophobic solvent (10.0 g), toluene, introduced on stage six (from the top), and the hydrophilic solvent or water wash (8.0 g) introduced on stage one (from the top). The final simulated raffinate (11.4 g—hydrophobic product) and extract (26.6 g—hydrophilic product) streams were subjected to GC and X-ray analysis to determine the compositions of the products. Results are given in Table 10.

TABLE 10

Simulated Extraction Results

| | Feed | Hydrophilic Solvent (%) | Hydrophobic Solvent (%) | Hydrophilic Product (%) | Hydrophobic Product (%) | % Recovery to extract |
|---|---|---|---|---|---|---|
| Toluene | 0.00 | | 100.0 | 0.23 | 37.32 | 0.26 |
| Water | 1.26 | 100.0 | | 69.53 | 8.37 | 78.07 |
| Triflic | 2.20 | | | 3.83 | <0.001 | >99.94 |
| G1 | 5.47 | | | 25.22 | 0.43 | 96.16 |
| A5 | 39.16 | | | 0.72 | 23.51 | 1.30 |
| A5GH | 50.58 | | | 0.06 | 29.86 | 0.09 |
| other | 1.33 | | | 0.41 | 0.51 | not determined |
| TOTAL | 100.0 | 100.0 | 100.0 | 100.0 | 100.0% | |

Example 65

Example 65 illustrates a continuous extraction demonstration of the recovery of triflic acid from a esters of glycolic and valeric acids feed stream derived from the hydrocarboxylation of formaldehyde using a hydrophilic solvent comprising 70 wt % G1, 30 wt % water and a hydrophobic solvent comprising 100 wt % toluene. This extraction was carried out in a Karr column comprising four jacketed glass column sections (15.9 mm inside diameter, each 501 mm in length) stacked on top of each other. Jacketed glass disengagement sections, 25.4 mm inside diameter and 200 mm in length, were attached to the top and bottom of the four extractor sections. The four column sections and two disengagement sections were joined together with Teflon O-ring gaskets (25 mm thickness) held together with bolted flanges to form the column body. Feed ports were fitted into each Teflon O-ring to allow change of feed locations. The total height of the resulting column was approximately 2.6 meters. Separate temperature-controlled heating baths were connected to the jacket of each disengagement zone and one bath to the combined four column sections to maintain the desired extraction temperature gradient.

Agitation in the column was supplied by an 3.2 mm diameter Hastelloy 276C impeller shaft fitted with seventy-seven Teflon plates, each with eight radial rectangular petals (to provide gaps for liquid flow paths), spaced 25 mm apart in the column sections. The impeller shaft was attached at the top of the extractor to an electric motor fitted with a concentric gear to convert rotational motion into reciprocal motion. The agitator stroke length (i.e., extent of vertical motion) was 19 mm, and varied from 200 to 350 strokes per minute.

Depending on the chosen continuous phase, the liquid-liquid phase interface was maintained in either the top or bottom disengagement section (in the top section if the less dense phase were continuous, bottom section if the more dense phase were continuous) by visual observation and manual manipulation of the underflow take-off pump.

Up to three feeds could be supplied to the column via piston pumps from independently temperature-controlled jacketed glass vessels of four liter, two liter, and two liter volumes, while the underflow (more dense) product and the top, overflow (less dense) product were collected in two-liter glass vessels. The top product collected by gravity overflow from the upper disengagement section, while the bottom product flow was controlled by a variable rate piston pump.

Feed locations are designated as follows from the top of the column to the bottom:

F1: Feed location between top disengagement zone and 1st column section

F2: Feed location between $3^{rd}$ and $4^{th}$ column sections

F3: Feed location between $4^{th}$ column section and bottom disengagement zone

The column was operated continuously for five hours. The feed was the combined crude hydrocarboxylation reactor product produced in Examples 137 and 138 discussed below. The crude hydrocarboxylation reactor product was fed at feed location F2, the hydrophilic solvent (70% glycolic acid and 30 wt % water) fed at F1 and the hydrophobic solvent fed at F3. The hydrophilic solvent to feed ratio was held at 0.124 to 1 on a mass basis, and the hydrophobic solvent to valerate-triflic feed mass ratio was held at 0.59. These conditions resulted in greater than 99.0% of the triflic acid being recovered in the polar extract (aqueous extract). Results from this extraction are tabulated below in Table 11. All values are in weight percent.

Triflic acid is recovered in the hydrophilic product stream (extract) at a rate of 99%. About 21.2% of all G1 moieties in the valerate-triflic feed and hydrophilic solvent were recovered to the hydrophobic raffinate phase, but subtracting out G1 entering in the hydrophilic solvent, the recovery of G1 moieties in the valerate-triflic feed rises to 68.3%. Furthermore, since the original feed to the hydrocarboxylation reaction resulting in the crude hydrocarboxylation product from Examples 137 and 138, contained G1, the extraction actually resulted in essentially complete recovery of new G1 moieties created in the reaction Examples 137 and 138. Thus, such an extraction is capable of fully separating triflic acid from valerate-glycolic esters and producing a concentrated triflic acid-glycolic acid stream suitable for recycle to hydrocarboxylation.

TABLE 11

| Karr Column Continuous Extraction | | | | | | | |
|---|---|---|---|---|---|---|---|
| | Feed | Hydrophilic Solvent | Hydrophobic Solvent | Hydrophilic Extract | Hydrophobic Raffinate | Mass Balance | Recovery to Extract |
| Triflic Acid | 2.93 | | | 7.74 | 0.023 | 100.4 | 99.0% |
| G1 | 13.30 | 70 | | 46.40 | 3.50 | 100.9 | 78.8% |
| DGA | 5.40 | | | 13.30 | 1 | 117.5 | 78.8% |
| A5 | 37 | | | 6.80 | 25.50 | 99.5 | 7.0% |
| A5GH | 26 | | | 6.30 | 17.50 | 99.5 | 9.2% |
| A5G2H | 7 | | | 1.40 | 5.07 | 104.8 | 7.2% |
| A5G3H | 2 | | | 0.40 | 1.26 | 92.1 | 8.2% |
| Others | 1.47 | | | 7.36 | 0.06 | 193.6 | 97.3% |
| Water | 4.90 | 30% | | 10.30 | 3.55 | 100.3 | 44.8% |
| Toluene | | | 100% | 3.60 | 42.54 | 99.0 | 2.3% |
| Total | 100.0 | 100.0 | 100% | 100.0 | 100.0 | 100.3 | |
| Flowrate, g/min | 10.5 | 1.3 | 6.2 | 3.95 | 14.1 | | |

The following examples illustrate the hydrocarboxylation of either MDA in acetic acid or MDP in propionic acid catalyzed by strongly acidic solid acid catalysts.

Example 66

MDA (methylene diacetate) or MDP (methylene dipropionate) used in the following Examples were produced from a refluxing mixture of paraformaldehyde and acetic or propionic anhydride in the presence of a small amount of sulfuric acid. The reactions were followed by gas chromatography. Upon completion of the reaction, sodium acetate (NaOAc) or propionate were added to the mixture to neutralize the sulfuric acid. The mixture was distilled to give 99% pure methylene dicarboxylate. The following procedure for methylene diacetate is exemplary: A 5 L round-bottom flask was fitted with a condenser, thermowell, overhead stirrer, inert gas bubbler, and heating mantle. To this flask was added 885 grams of paraformaldehyde followed by 3,324 mL of acetic anhydride. The mixture was then stirred at room temperature and 12 mL of concentrated sulfuric acid was added. An exotherm heated the solution to approximately 80° C. and then the heating mantle was turned on. The mixture was held at reflux for almost 10 hours and sampled periodically to check for completion by gas chromatography. Upon completion, 35 g of NaOAc was added to the mixture to neutralize the sulfuric acid. The mixture was then transferred to another flask along with the NaOAc and pure MDA was distilled.

Example 67

A 50 mL Hastelloy 276C high pressure autoclave was fitted with an impeller, gas inlet tube, sample tube, and thermowell.

The autoclave was heated with a heating block, with temperature control provided by feedback via a thermocouple in the autoclave thermowell. Pure carbon monoxide gas (>99.9%) was fed to the autoclave via a high pressure regulator. The autoclave was charged with 20% W-heteropoly/silica catalyst (1.48 g) propionic acid (12.28 g, 0.16 mol) and MDP (14.1 g, 0.08 mol) and water (1.4 g, 0.08 mol) and sealed. The autoclave was secured to the stand and the system was pressurized with 200 psig nitrogen and vented. This purging procedure was repeated two times. The autoclave was then purged with carbon monoxide and pressurized to 200 psig carbon monoxide. The temperature in the autoclave was increased to 140° C. Upon reaching 140° C., the pressure in the autoclave was increased to 1,000 psig carbon monoxide. The reaction was held at these conditions for 2 hours and then cooled to room temperature and vented. Finally the autoclave was purged with nitrogen and unloaded. The reaction contents were analyzed by GC. Results are shown in Table 12.

Examples 68-83

The procedure of Example 67 was repeated using either MDP/propionic acid or MDA/acetic acid and water at target equivalents of 1 eq. of MDA(MDP), 2 eq. acetic (propionic) acid, and 1 eq. water at a reaction pressure of 1000 psig carbon monoxide. The examples were run with the solid catalyst and corresponding loading, at the temperature, and for the holding time shown in Table 12. Calculated yields are also given in Table 12.

TABLE 12

Hydrocarboxylations of Methylene Diacetate (MDA) or Methylene Dipropionate (MDP) Catalyzed by Strongly Acidic Solid Acid Catalysts.

| EX | | catalyst | loading (wt %) | temp (° C.) | time (h) | yield (%) |
|---|---|---|---|---|---|---|
| 67 | MDP | 20% W-heteropoly/silica | 5 | 140 | 2 | 6.5 |
| 68 | MDP | SiO$_2$/Al$_2$O$_3$ | 5 | 140 | 2 | 2.0 |
| 69 | MDA | K10 | 5 | 140 | 2 | 3.8 |
| 70 | MDA | AMBERLYST 70 | 5 | 140 | 2 | 18.8 |
| 71 | MDA | SAC-13 | 9 | 140 | 1 | 47.8 |
| 72 | MDA | SAC-13 | 9 | 160 | 1 | 69.8 |
| 73 | MDA | SAC-13 | 9 | 180 | 1 | 78.8 |
| 74 | MDA | Nafion NR50 | 5 | 140 | 2 | 69.4 |
| 75 | MDA | SAC-13 | 15 | 160 | 1 | 98.6 |
| 76 | MDA | polymer-bound pTSA | 5 | 140 | 2 | 66 |
| 77 | MDA | AMBERLYST 36 | 5 | 140 | 2 | 77 |
| 78 | MDA | SMOPEX (4% crosslinking) | 5 | 140 | 3 | 65 |
| 79 | MDA | SMOPEX (8% crosslinking) | 5 | 160 | 2 | 70 |
| 80 | MDA | SMOPEX (12% crosslinking) | 5 | 180 | 2 | 66 |
| 81 | MDP | AMBERLYST 36 | 5 | 140 | 2 | 86 |
| 82 | MDP | SAC-13 | 10 | 140 | 2 | 76 |
| 83 | MDP | SMOPEX (4% crosslinking) | 5 | 140 | 2 | 68 |

Examples 84

A 50 mL Hastelloy 276C high pressure autoclave was fitted with an impeller, gas inlet tube, sample tube, and thermowell. The autoclave was heated with a heating block, with temperature control provided by feedback via a thermocouple in the autoclave thermowell. Pure carbon monoxide gas (>99.9%) was fed to the autoclave via a high pressure regulator. The autoclave was charged with AMBERLYST 36 D catalyst (1.43 g), propionic acid (12.3 g, 0.166 mol), MDP (14.1 g, 0.088 mol), and water (1.5 g, 0.083 mol) and sealed. The autoclave was secured to the stand and the system was pressurized with 200 psig nitrogen and vented. This purging procedure was repeated two times. The autoclave was then purged with carbon monoxide and pressurized to 500 psig carbon monoxide. The temperature in the autoclave was increased to 140° C. Upon reaching 140° C., the pressure in the autoclave was increased to 1,000 psig carbon monoxide. The reaction was held at these conditions for 2 hours and then cooled to room temperature and vented. Finally the autoclave was purged with nitrogen and unloaded. The reaction contents were analyzed by GC. The results are shown in Table 13.

Examples 85-91

Example 84 was repeated with the catalyst and catalyst loading and amount of propionic acid and water given in Table 13. Each reaction was run at 1000 psig carbon monoxide and at the temperature and for the time indicated in Table 13. Yield to desired products and selectivity are also given in Table 13.

TABLE 13

Hydrocarboxylations of MDP

| Ex. | Catalyst | Loading (wt %) | A3 (eq) | Water (eq) | Temp (° C.) | Time (h) | Yield (%) | Select. (%) |
|---|---|---|---|---|---|---|---|---|
| 84 | AMBERLYST 36 D | 5 | 2.0 | 1.0 | 140 | 2 | 96 | 96 |
| 85 | AMBERLYST 36 D | 8 | 0.14 | 1.1 | 140 | 2 | 89 | 94 |
| 86 | AMBERLYST 36 D | 5 | 2.1 | 1 | 140 | 2 | 86 | 96 |
| 87 | AMBERLYST 36 D | 5 | 1.1 | 1 | 140 | 2 | 78 | 95 |
| 88 | AMBERLYST 36 D | 5 | 0.15 | 1 | 140 | 2 | 72 | 94 |
| 89 | AMBERLYST 36 D | 5 | 2 | 0.05 | 140 | 2 | 2 | 28 |
| 90 | AMBERLYST 36 D | 5 | 2 | 0.05 | 90 | 2 | 3 | 5 |
| 91 | AMBERLYST 36 D | 5 | 2 | 0.5 | 140 | 2 | 16 | 66 |

The following examples illustrate the hydrocarboxylation of MDA in acetic acid catalyzed by various strongly acidic homogeneous catalysts. MDA was prepared as described above in Example 66.

Example 92

To a Hastelloy 276C 300 mL autoclave equipped with a liquid sampling loop and a high pressure addition funnel was added acetic acid (60.05 g, 1.0 mol), water (9.0 g, 0.5 mol), and trifluoromethanesulfonic acid catalyst (0.375 g, 2.5 mmol). The autoclave was heated with a heating block, with temperature control provided by feedback via a thermocouple in the autoclave thermowell. Pure carbon monoxide gas (>99.9%) was fed to the autoclave via a high pressure regulator. The MDA (66.26 g, 0.5 mol) was added to the addition funnel (blowcase). The autoclave was sealed, flushed with CO and heated to 140° C. under 100 psig carbon monoxide. The addition funnel containing the MDA was heated to 100° C. Upon reaching 140° C. in the autoclave, the MDA was charged to the autoclave by pressurizing the addition funnel. Immediately upon completing the liquid addition, a sample was removed from the autoclave (time zero) and the pressure was adjusted to 1000 psig CO. The temperature and pressure were maintained using pure carbon monoxide for the duration of the 4 hour reaction. Samples were removed from the autoclave at 15 min, 30 min, 45 min, 60 min, 120 min, 180 min and 240 min. The samples were analyzed by GC and HPLC. Final conversion and selectivity is given in Table 14.

Examples 93-96

Example 92 was repeated except the acid catalyst and amount were as given in Table 14. 2.5 mmol of acid catalyst was used in each case. The final MDA conversions and selectivities are given in Table 14.

TABLE 14

Hydrocarboxylation of MDA in Acetic Acid with a Homogeneous Strong Acid Catalyst.

| Ex. | Catalyst | Catalyst charge (g) | MDA Conversion | MDA Selectivity |
|---|---|---|---|---|
| 92 | trifluoromethanesulfonic acid | 0.375 | 99 | 96 |
| 93 | tetrafluoroethanesulfonic acid | 0.455 | 96 | 96 |
| 94 | bis(trifluoromethane) sulfonylamide | 0.70 | 99 | 95 |
| 95 | nonafluorobutanesulfonic acid | 0.75 | 99 | 95 |
| 96 | sulfuric acid | 0.256 | 81 | 53 |

The following examples illustrate the effect of feed water content, temperature, pressure, and catalyst level on the hydrocarboxylation of trioxane or paraformaldehyde with valeric acid and glycolic acid as solvents/reactants and triflic acid as catalyst.

Example 97

The continuous hydrocarboxylation was carried out using a reactor system containing Hastelloy 276C autoclave (125 ml nominal volume) and associated feed and product storage equipment. The high pressure autoclave was fitted with a hollow shaft Rushton turbine impeller (for gas introduction and dispersion), baffles, thermowell, gas inlet tube, and sip tube to maintain liquid level at approximately 90 ml and to provide an exit for product effluent. The autoclave was heated electrically by a band heater, with temperature control provided by feedback via a K-type thermocouple in the autoclave thermowell.

Pure carbon monoxide gas (>99.9%) was fed to the autoclave via a high pressure flow controller. The gas entered the body of the autoclave via groves in the impeller bearings. The off gas flow rate was monitored by a dry bubble-type flow meter. The flow rates of the two liquid feeds were controlled to a precision of 0.001 ml/min with double-barreled 500 ml high-precision syringe pumps connected to stirred feed vessels.

Reactor effluent passed through heated Hastelloy tubing, an automatic pressure control valve (research control valve), and into a 1.0 L heatable Hastelloy collection vessel. The effluent collection vessel was fitted with a chilled coiled condenser. The gas outlet from the effluent tank was connected to a manual back pressure regulator to maintain vessel pressure at 40-100 psig. Temperatures, pressures, and other relevant system parameters were recorded automatically by a distributed control system.

Feed 1 (0.4 g/min) and Feed 2 (0.39 g/min), having the composition given in Table 15 were fed to the reactor. Carbon monoxide was fed at a rate of 998 SCCM as noted in Table 16. The reaction was run at a pressure of 1500 psig and a temperature of 170° C. with a residence time of 85 minutes. Table 16 also gives feed molar ratios and the source of formaldehyde. For Example 107 the source was trioxane.

Samples of the hydrocarboxylation reaction were analyzed by HPLC. Conversion, space-time yield, and selectivity of reacted formaldehyde to end products are summarized in Table 17. Any glycolic acid fed was subtracted out for conversion and yield calculations. Methanol was present as free methanol, methyl glycolate, and methyl valerate, and was converted to free methanol, glycolic acid, and valeric acid by the analytical method.

Examples 98-143

Example 97 was repeated with the liquid feeds given in Table 15, the carbon monoxide flow rate, source of formaldehyde, feed molar ratios, pressure, temperature, residence time given in Table 16. Conversion, space-time yield, and selectivity of reacted formaldehyde to end products are summarized in Table 17.

TABLE 15

Feed 1 and Feed 2: Rates and Compositions

| Ex # | Feed 1 g/min | Feed 1, mass % | | | | | Feed 2 g/min | Feed 2 mass % | |
| | | F0 | A5 | G1 | water | Triflic | | A5 | Triflic |
|---|---|---|---|---|---|---|---|---|---|
| 97 | 0.40 | 21.1 | 71.9 | 0.0 | 3.8 | 3.2 | 0.39 | 100.00 | 0.00 |
| 98 | 0.39 | 21.1 | 71.9 | 0.0 | 3.8 | 3.2 | 0.39 | 100.00 | 0.00 |
| 99 | 0.39 | 21.1 | 71.9 | 0.0 | 3.8 | 3.2 | 0.39 | 100.00 | 0.00 |
| 100 | 0.39 | 21.1 | 71.9 | 0.0 | 3.8 | 3.2 | 0.39 | 100.00 | 0.00 |
| 101 | 0.39 | 21.1 | 71.9 | 0.0 | 3.8 | 3.2 | 0.39 | 100.00 | 0.00 |
| 102 | 0.39 | 21.1 | 71.9 | 0.0 | 3.8 | 3.2 | 0.39 | 100.00 | 0.00 |
| 103 | 0.39 | 21.1 | 71.9 | 0.0 | 3.8 | 3.2 | 0.39 | 100.00 | 0.00 |
| 104 | 0.61 | 21.1 | 71.9 | 0.0 | 3.8 | 3.2 | 0.62 | 100.00 | 0.00 |
| 105 | 0.61 | 21.1 | 71.9 | 0.0 | 3.8 | 3.2 | 0.62 | 100.00 | 0.00 |
| 106 | 0.39 | 21.1 | 71.9 | 0.0 | 3.8 | 3.2 | 0.39 | 100.00 | 0.00 |
| 107 | 0.61 | 21.1 | 71.9 | 0.0 | 3.8 | 3.2 | 0.62 | 100.00 | 0.00 |
| 108 | 0.39 | 21.8 | 74.2 | 0.0 | 3.9 | 0.0 | 0.39 | 95.78 | 4.22 |
| 109 | 0.39 | 21.8 | 74.2 | 0.0 | 3.9 | 0.0 | 0.39 | 95.78 | 4.22 |
| 110 | 0.39 | 21.8 | 74.2 | 0.0 | 3.9 | 0.0 | 0.39 | 95.78 | 4.22 |
| 111 | 0.39 | 21.8 | 74.2 | 0.0 | 3.9 | 0.0 | 0.39 | 95.78 | 4.22 |
| 112 | 0.39 | 21.8 | 74.2 | 0.0 | 3.9 | 0.0 | 0.39 | 95.78 | 4.22 |
| 113 | 0.64 | 26.8 | 68.4 | 0.0 | 4.8 | 0.0 | 0.17 | 85.01 | 14.99 |
| 114 | 0.64 | 26.8 | 68.4 | 0.0 | 4.8 | 0.0 | 0.17 | 85.01 | 14.99 |
| 115 | 0.64 | 26.8 | 68.4 | 0.0 | 4.8 | 0.0 | 0.17 | 85.01 | 14.99 |
| 116 | 0.64 | 26.8 | 68.4 | 0.0 | 4.8 | 0.0 | 0.17 | 85.01 | 14.99 |
| 117 | 0.64 | 26.8 | 68.4 | 0.0 | 4.8 | 0.0 | 0.17 | 85.01 | 14.99 |
| 118 | 0.68 | 23.7 | 0.0 | 60.0 | 9.9 | 6.4 | 0.36 | 100.00 | 0.00 |

TABLE 15-continued

Feed 1 and Feed 2: Rates and Compositions

| | | Feed 1, mass % | | | | | | Feed 2 mass % | |
| --- | --- | --- | --- | --- | --- | --- | --- | --- | --- |
| Ex # | Feed 1 g/min | F0 | A5 | G1 | water | Triflic | Feed 2 g/min | A5 | Triflic |
| 119 | 0.68 | 23.7 | 0.0 | 60.0 | 9.9 | 6.4 | 0.36 | 100.00 | 0.00 |
| 120 | 0.68 | 23.7 | 0.0 | 60.0 | 9.9 | 6.4 | 0.36 | 100.00 | 0.00 |
| 121 | 0.68 | 23.7 | 0.0 | 60.0 | 9.9 | 6.4 | 0.32 | 100.00 | 0.00 |
| 122 | 0.68 | 23.7 | 0.0 | 60.0 | 9.9 | 6.4 | 0.36 | 100.00 | 0.00 |
| 123 | 0.68 | 23.7 | 0.0 | 60.0 | 9.9 | 6.4 | 0.36 | 100.00 | 0.00 |
| 124 | 0.43 | 34.0 | 0.0 | 51.7 | 14.3 | 0.0 | 0.52 | 92.93 | 7.07 |
| 125 | 0.43 | 34.0 | 0.0 | 51.7 | 14.3 | 0.0 | 0.52 | 92.93 | 7.07 |
| 126 | 0.43 | 34.0 | 0.0 | 51.7 | 14.3 | 0.0 | 0.52 | 92.93 | 7.07 |
| 127 | 0.43 | 34.0 | 0.0 | 51.7 | 14.3 | 0.0 | 0.52 | 92.93 | 7.07 |
| 128 | 0.43 | 34.0 | 0.0 | 51.7 | 14.3 | 0.0 | 0.52 | 92.93 | 7.07 |
| 129 | 0.43 | 34.0 | 0.0 | 51.7 | 14.3 | 0.0 | 0.52 | 92.93 | 7.07 |
| 130 | 0.43 | 34.0 | 0.0 | 51.7 | 14.3 | 0.0 | 0.52 | 92.93 | 7.07 |
| 131 | 0.65 | 25.1 | 0.0 | 63.6 | 4.5 | 6.8 | 0.38 | 100.00 | 0.00 |
| 132 | 0.65 | 25.1 | 0.0 | 63.6 | 4.5 | 6.8 | 0.38 | 100.00 | 0.00 |
| 133 | 0.65 | 25.1 | 0.0 | 63.6 | 4.5 | 6.8 | 0.38 | 100.00 | 0.00 |
| 134 | 0.65 | 25.1 | 0.0 | 63.6 | 4.5 | 6.8 | 0.38 | 100.00 | 0.00 |
| 135 | 0.65 | 25.1 | 0.0 | 63.6 | 4.5 | 6.8 | 0.38 | 100.00 | 0.00 |
| 136 | 0.65 | 25.1 | 0.0 | 63.6 | 4.5 | 6.8 | 0.38 | 100.00 | 0.00 |
| 137 | 0.47 | 32.5 | 0.0 | 61.7 | 5.8 | 0.0 | 0.54 | 92.61 | 7.39 |
| 138 | 0.47 | 32.5 | 0.0 | 61.7 | 5.8 | 0.0 | 0.54 | 92.61 | 7.39 |
| 139 | 0.47 | 32.5 | 0.0 | 61.7 | 5.8 | 0.0 | 0.54 | 92.61 | 7.39 |
| 140 | 0.47 | 32.5 | 0.0 | 61.7 | 5.8 | 0.0 | 0.54 | 92.61 | 7.39 |
| 141 | 0.47 | 32.5 | 0.0 | 61.7 | 5.8 | 0.0 | 0.54 | 92.61 | 7.39 |
| 142 | 0.47 | 32.5 | 0.0 | 61.7 | 5.8 | 0.0 | 0.54 | 92.61 | 7.39 |
| 143 | 0.47 | 32.5 | 0.0 | 61.7 | 5.8 | 0.0 | 0.54 | 92.61 | 7.39% |

TABLE 16

Overall Feed Molar Ratios and Reaction Conditions

| | CO Flow | F0 | Feed Molar Ratio | | | | | Press | Temp | Res Time |
| --- | --- | --- | --- | --- | --- | --- | --- | --- | --- | --- |
| Ex | SCCM | Type | HFR | A5 | G1 | water | Triflic | Psig | Celsius | min |
| 97 | 998.0 | Trioxane | 1.0 | 2.0 | 0.0 | 0.3 | 0.030 | 1500 | 170 | 85 |
| 98 | 998.0 | Trioxane | 1.0 | 2.0 | 0.0 | 0.3 | 0.030 | 1001 | 170 | 87 |
| 99 | 998.0 | Trioxane | 1.0 | 2.0 | 0.0 | 0.3 | 0.030 | 1498 | 160 | 87 |
| 100 | 998.0 | Trioxane | 1.0 | 2.0 | 0.0 | 0.30 | 0.030 | 1501 | 150 | 87 |
| 101 | 998.0 | Trioxane | 1.0 | 2.0 | 0.0 | 0.30 | 0.030 | 747 | 160 | 87 |
| 102 | 998.0 | Trioxane | 1.0 | 2.0 | 0.0 | 0.30 | 0.030 | 997 | 160 | 87 |
| 103 | 998.0 | Trioxane | 1.0 | 2.0 | 0.0 | 0.30 | 0.030 | 1500 | 170 | 87 |
| 104 | 998.0 | Trioxane | 1.0 | 2.0 | 0.0 | 0.30 | 0.030 | 749 | 150 | 55 |
| 105 | 998.0 | Trioxane | 1.0 | 2.0 | 0.0 | 0.30 | 0.030 | 750 | 140 | 55 |
| 106 | 998.0 | Trioxane | 1.0 | 2.0 | 0.0 | 0.30 | 0.030 | 753 | 170 | 87 |
| 107 | 998.0 | Trioxane | 1.0 | 2.0 | 0.0 | 0.30 | 0.030 | 751 | 150 | 55 |
| 108 | 998.0 | Trioxane | 1.0 | 2.0 | 0.0 | 0.30 | 0.030 | 1501 | 143 | 87 |
| 109 | 998.0 | Trioxane | 1.0 | 2.0 | 0.0 | 0.30 | 0.030 | 1495 | 160 | 87 |
| 110 | 998.0 | Trioxane | 1.0 | 2.0 | 0.0 | 0.30 | 0.030 | 1498 | 170 | 87 |
| 111 | 998.0 | Trioxane | 1.0 | 2.0 | 0.0 | 0.30 | 0.030 | 1500 | 170 | 87 |
| 112 | 998.0 | Trioxane | 1.0 | 2.0 | 0.0 | 0.30 | 0.030 | 1499 | 170 | 87 |
| 113 | 998.0 | Trioxane | 1.0 | 1.0 | 0.0 | 0.30 | 0.030 | 1498 | 170 | 87 |
| 114 | 998.0 | Trioxane | 1.0 | 1.0 | 0.0 | 0.30 | 0.030 | 1003 | 170 | 87 |
| 115 | 998.0 | Trioxane | 1.0 | 1.0 | 0.0 | 0.30 | 0.030 | 499 | 170 | 87 |
| 116 | 998.0 | Trioxane | 1.0 | 1.0 | 0.0 | 0.30 | 0.030 | 999 | 160 | 87 |
| 117 | 998.0 | Trioxane | 1.0 | 1.0 | 0.0 | 0.30 | 0.030 | 506 | 165 | 87 |
| 118 | 998.0 | PF | 1.0 | 0.7 | 1.0 | 0.70 | 0.054 | 1497 | 180 | 80 |
| 119 | 998.0 | PF | 1.0 | 0.7 | 1.0 | 0.70 | 0.054 | 1503 | 180 | 80 |
| 120 | 998.0 | PF | 1.0 | 0.7 | 1.0 | 0.70 | 0.054 | 1497 | 180 | 80 |
| 121 | 998.0 | PF | 1.0 | 0.7 | 1.0 | 0.70 | 0.054 | 1498 | 180 | 83 |
| 122 | 998.0 | PF | 1.0 | 0.7 | 1.0 | 0.70 | 0.054 | 1504 | 180 | 80 |
| 123 | 998.0 | PF | 1.0 | 0.7 | 1.0 | 0.70 | 0.054 | 1504 | 180 | 80 |
| 124 | 998.0 | PF | 1.0 | 1.0 | 0.6 | 0.70 | 0.054 | 1492 | 180 | 80 |
| 125 | 998.0 | PF | 1.0 | 1.0 | 0.6 | 0.70 | 0.054 | 1003 | 180 | 80 |
| 126 | 998.0 | PF | 1.0 | 1.0 | 0.6 | 0.70 | 0.054 | 500 | 180 | 80 |
| 127 | 998.0 | PF | 1.0 | 1.0 | 0.6 | 0.70 | 0.054 | 995 | 170 | 80 |
| 128 | 998.0 | PF | 1.0 | 1.0 | 0.6 | 0.70 | 0.054 | 502 | 170 | 80 |
| 129 | 998.0 | PF | 1.0 | 1.0 | 0.6 | 0.70 | 0.054 | 1000 | 160 | 80 |
| 130 | 998.0 | PF | 1.0 | 1.0 | 0.6 | 0.70 | 0.054 | 498 | 160 | 80 |
| 131 | 498.0 | PF | 1.0 | 0.7 | 1.0 | 0.30 | 0.054 | 1507 | 170 | 80 |
| 132 | 498.0 | PF | 1.0 | 0.7 | 1.0 | 0.30 | 0.054 | 1499 | 180 | 80 |

TABLE 16-continued

Overall Feed Molar Ratios and Reaction Conditions

| Ex | CO Flow SCCM | F0 Type | HFR | A5 | G1 | water | Triflic | Press Psig | Temp Celsius | Res Time min |
|---|---|---|---|---|---|---|---|---|---|---|
| 133 | 498.0 | PF | 1.0 | 0.7 | 1.0 | 0.30 | 0.054 | 1503 | 180 | 80 |
| 134 | 498.0 | PF | 1.0 | 0.7 | 1.0 | 0.30 | 0.054 | 1498 | 180 | 80 |
| 135 | 498.0 | PF | 1.0 | 0.7 | 1.0 | 0.30 | 0.054 | 1003 | 160 | 80 |
| 136 | 498.0 | PF | 1.0 | 0.7 | 1.0 | 0.30 | 0.054 | 1501 | 170 | 80 |
| 137 | 498.0 | PF | 1.0 | 1.0 | 0.8 | 0.30 | 0.054 | 1500 | 180 | 76 |
| 138 | 498.0 | PF | 1.0 | 1.0 | 0.8 | 0.30 | 0.054 | 999 | 180 | 76 |
| 139 | 498.0 | PF | 1.0 | 1.0 | 0.8 | 0.30 | 0.054 | 500 | 180 | 76 |
| 140 | 498.0 | PF | 1.0 | 1.0 | 0.8 | 0.30 | 0.054 | 999 | 170 | 76 |
| 141 | 498.0 | PF | 1.0 | 1.0 | 0.8 | 0.30 | 0.054 | 500 | 170 | 76 |
| 142 | 498.0 | PF | 1.0 | 1.0 | 0.8 | 0.30 | 0.054 | 1004 | 160 | 76 |
| 143 | 498.0 | PF | 1.0 | 1.0 | 0.8 | 0.30 | 0.054 | 500 | 160 | 76 |

TABLE 17

Selectivity, Conversion, and Space-Time Yield Results

| Example | % F0 Conversion | Space Time Yield gmol/l-hr | Molar Selectivity G1 | A1 | DG | MGH | MeOH |
|---|---|---|---|---|---|---|---|
| 97 | 94.7 | 1.51 | 96.42 | 1.02 | 1.55 | 0.00 | 1.02 |
| 98 | 93.0 | 1.44 | 96.71 | 0.93 | 1.42 | 0.00 | 0.93 |
| 99 | 93.5 | 1.42 | 96.41 | 1.23 | 1.13 | 0.00 | 1.23 |
| 100 | 92.5 | 0.93 | 96.22 | 1.36 | 1.06 | 0.00 | 1.36 |
| 101 | 87.1 | 1.36 | 96.17 | 1.41 | 0.80 | 0.43 | 1.19 |
| 102 | 90.3 | 1.32 | 96.92 | 1.09 | 0.91 | 0.00 | 1.09 |
| 103 | 96.3 | 1.37 | 96.90 | 0.87 | 1.36 | 0.00 | 0.87 |
| 104 | 75.3 | 1.59 | 91.30 | 3.85 | 0.99 | 0.00 | 3.85 |
| 105 | 56.3 | 1.22 | 85.32 | 7.16 | 0.10 | 0.50 | 6.91 |
| 106 | 89.4 | 1.41 | 96.55 | 1.05 | 1.34 | 0.00 | 1.05 |
| 107 | 67.5 | 1.89 | 92.15 | 3.56 | 0.72 | 0.00 | 3.56 |
| 108 | 86.2 | 1.42 | 94.31 | 2.33 | 0.98 | 0.12 | 2.26 |
| 109 | 91.3 | 1.55 | 96.12 | 1.26 | 1.36 | 0.00 | 1.26 |
| 110 | 93.5 | 1.60 | 96.32 | 1.05 | 1.58 | 0.00 | 1.05 |
| 111 | 95.2 | 1.59 | 96.10 | 1.13 | 1.64 | 0.00 | 1.13 |
| 112 | 90.9 | 1.55 | 96.71 | 0.93 | 1.42 | 0.00 | 0.93 |
| 113 | 62.6 | 1.79 | 91.65 | 2.07 | 4.07 | 0.19 | 1.97 |
| 114 | 54.5 | 1.84 | 91.64 | 0.47 | 7.42 | 0.00 | 0.47 |
| 115 | 86.6 | 2.72 | 92.16 | 2.45 | 2.62 | 0.56 | 2.17 |
| 116 | 84.4 | 2.84 | 93.10 | 1.93 | 3.03 | 0.00 | 1.93 |
| 117 | 80.7 | 2.56 | 94.18 | 1.38 | 2.88 | 0.37 | 1.19 |
| 118 | 90.2 | 2.24 | 89.72 | 2.00 | 5.69 | 0.73 | 1.64 |
| 119 | 90.4 | 2.49 | 90.79 | 1.67 | 5.85 | 0.00 | 1.67 |
| 120 | 90.1 | 2.69 | 94.24 | 1.47 | 2.82 | 0.00 | 1.47 |
| 121 | 89.1 | 2.66 | 92.90 | 1.83 | 3.07 | 0.31 | 1.68 |
| 122 | 90.0 | 2.47 | 93.07 | 1.67 | 3.10 | 0.72 | 1.31 |
| 123 | 90.2 | 2.60 | 93.35 | 1.69 | 2.94 | 0.66 | 1.36 |
| 124 | 91.7 | 2.37 | 93.41 | 1.71 | 3.11 | 0.11 | 1.66 |
| 125 | 85.7 | 2.13 | 91.14 | 3.20 | 2.01 | 0.90 | 2.75 |
| 126 | 76.4 | 1.44 | 79.78 | 8.41 | 2.09 | 1.83 | 7.49 |
| 127 | 75.5 | 2.40 | 90.60 | 3.53 | 2.16 | 0.36 | 3.35 |
| 128 | 59.9 | 1.78 | 83.27 | 7.20 | 1.43 | 0.85 | 6.78 |
| 129 | 66.5 | 0.92 | 70.09 | 11.5 | 2.31 | 7.69 | 7.75 |
| 130 | 53.4 | 0.57 | 58.03 | 20.1 | 0.93 | 0.86 | 19.68 |
| 131 | 89.5 | 2.25 | 89.86 | 2.62 | 3.94 | 1.49 | 1.87 |
| 132 | 94.9 | 2.87 | 92.05 | 1.47 | 4.53 | 0.79 | 1.07 |
| 133 | 95.2 | 2.46 | 91.01 | 1.71 | 4.98 | 0.92 | 1.25 |
| 134 | 92.9 | 2.46 | 92.89 | 1.43 | 4.02 | 0.37 | 1.24 |
| 135 | 83.0 | 1.92 | 89.48 | 3.19 | 3.45 | 1.21 | 2.58 |
| 136 | 92.5 | 2.53 | 91.90 | 1.63 | 4.28 | 0.72 | 1.27 |
| 137 | 93.0 | 2.62 | 93.77 | 1.51 | 2.95 | 0.53 | 1.24 |
| 138 | 93.6 | 2.82 | 94.21 | 1.37 | 2.96 | 0.17 | 1.29 |
| 139 | 87.1 | 2.35 | 89.56 | 3.53 | 2.91 | 0.81 | 3.13 |
| 140 | 90.4 | 2.48 | 93.64 | 1.72 | 2.84 | 0.00 | 1.72 |
| 141 | 80.0 | 2.12 | 87.08 | 4.91 | 2.46 | 0.88 | 4.47 |
| 142 | 82.0 | 2.28 | 90.50 | 3.24 | 2.44 | 1.13 | 2.68 |
| 143 | 71.6 | 2.05 | 86.67 | 5.24 | 2.30 | 0.48 | 5.00 |

These examples illustrate the effect of feed water content, temperature, pressure, and catalyst level on the hydrocarboxylation of formaldehyde (trioxane) with triflic acid as catalyst, with n-butyric acid and glycolic acid as solvent/reactant.

Examples 144-147

Example 97 was repeated with only one feed at 0.91 g/min. The feed contained 14.6 wt % paraformaldehyde, 6.2% water, 28.8 wt % butyric acid, 48.2 wt % glycolic acid, and 2.2 wt % triflic acid. The feed molar ratio was paraformaldehyde (1.0), water (0.7), glycolic acid (1.5), and triflic acid (0.03). The hold-up time was 95 minutes. The feed rate of carbon monoxide was 498 SCCM. The operating pressure and temperature, along with conversion, space-time yield, and selectivity of reacted formaldehyde to end products are summarized in Table 18.

TABLE 18

Reactor Conditions, Selectivity, Conversion, and Space-Time Yield Results

| Ex | Temp Celsius | Pressure psig | % F0 Conversion | Molar Selectivity G1 | A1 | MeOH | MGH | DG | Space-Time Yield gmol/l-hr |
|---|---|---|---|---|---|---|---|---|---|
| 144 | 150 | 935 | 40.1 | 70.1 | 13.9 | 13.9 | 0.0 | 2.2 | 1.04 |
| 145 | 170 | 1199 | 71.2 | 83.3 | 5.6 | 5.6 | 1.5 | 4.1 | 2.08 |
| 146 | 190 | 1199 | 88.3 | 89.6 | 1.8 | 1.8 | 1.6 | 5.2 | 2.91 |
| 147 | 170 | 1745 | 77.5 | 88.0 | 3.6 | 3.6 | 0.8 | 3.8 | 2.38 |

The following examples illustrate the effect of feed water content, temperature, pressure and catalyst level on the hydrocarboxylation of methylene diacetate with triflic acid as catalyst.

Examples 148-153

Example 97 was repeated but with MDA as the source of formaldehyde and at the feed rates and compositions noted in Table 19. In these experiments moles of MDA represent the formaldehyde equivalent, while acetic acid equivalents are calculated as the sum of free acetic acid fed and two times the MDA molar flow rate. The feed molar ratios, temperature, pressure, and hold-up time are given in Table 20. Conversion, space-time yield, and selectivity of reacted formaldehyde to end products are summarized in Table 21. All methanol was present as methyl acetate, and was also converted to free methanol and acetic acid by the analytical method.

TABLE 19

Feed 1 and 2 Rates and Compositions

| | Feed 1 | Feed 1, mass % | | | Feed 2 | Feed 2 mass % | | |
|---|---|---|---|---|---|---|---|---|
| Ex | g/min | MDA | A2 | water | g/min | A2 | water | Triflic |
| 148 | 0.69 | 100 | 0 | 0 | 0.71 | 86.7 | 1.3 | 0.30 |
| 149 | 0.69 | 100 | 0 | 0 | 0.79 | 69.5 | 29.2 | 1.30 |
| 150 | 0.69 | 100 | 0 | 0 | 0.79 | 69.5 | 29.2 | 1.30 |
| 151 | 0.69 | 100 | 0 | 0 | 0.79 | 69.5 | 29.2 | 1.30 |
| 152 | 1.10 | 56.4 | 7.7 | 35.9 | 0.32 | 99 | 0 | 1 |
| 153 | 0.03 | 56.4 | 7.7 | 35.0 | 0.32 | 96 | 0 | 4 |

TABLE 20

Overall Feed Ratios and Reaction Conditions

| Ex | Feed Molar Ratio F0 | water | A2 | Triflic | Temp Celsius | Press psig | Res Time minutes |
|---|---|---|---|---|---|---|---|
| 148 | 1.0 | 1.2 | 3.8 | 0.002 | 190 | 650 | 70 |
| 149 | 1.0 | 1.4 | 3.0 | 0.007 | 200 | 600 | 67 |
| 150 | 1.0 | 1.4 | 3.0 | 0.007 | 190 | 600 | 67 |
| 151 | 1.0 | 1.4 | 3.0 | 0.007 | 180 | 600 | 67 |
| 152 | 1.0 | 1.0 | 4.5 | 0.005 | 190 | 1300 | 69 |
| 153 | 1.0 | 1.0 | 4.5 | 0.020 | 170 | 1300 | 73 |

TABLE 21

Selectivity, Conversion, and Space-Time Yield Results

| Ex | % HFr Conv | Molar Selectivity G1 | A1 | MeOH | MGH | DG | Space-Time Yield gmol/l-hr |
|---|---|---|---|---|---|---|---|
| 148 | 70 | 95.8 | 1.75 | 1.75 | 0.00 | 0.85 | 2.20 |
| 149 | 75 | 90.8 | 1.7 | 1.7 | 0.00 | 5.8 | 2.00 |
| 150 | 70 | 94.2 | 1.5 | 1.5 | 0.00 | 2.8 | 2.00 |
| 151 | 50 | 92.9 | 1.8 | 1.7 | 0.3 | 3.1 | 1.20 |
| 152 | 77 | 93.1 | 1.7 | 1.3 | 0.7 | 3.1 | 2.60 |
| 153 | 95 | 93.3 | 1.7 | 1.4 | 0.7 | 2.9 | 2.80 |

The following examples illustrate the effect of feed water content, temperature, pressure, and catalyst level on the hydrocarboxylation of paraformaldehyde with sulfuric acid as catalyst.

Examples 154-159

Example 97 was repeated using only one feed stream with the feed rate and compositions shown in Table 22. The feed mixture was prepared by mixing, water, $H_2SO_4$ and HGH in a tank heated to 60° C. Paraformaldehyde was added with stirring until complete dissolution occurred. The feed was kept at 60° C. throughout the reaction period to ensure no solid formaldehyde precipitated. The operating conditions along with reaction pressure, temperature and residence time are summarized in Tables 22 and 23.

Conversion, space-time yield, and selectivity of reacted formaldehyde to end products are summarized in Table 24. During analysis, glycolic acid oligomers and other forms of glycolic acid were hydrolyzed and converted to free monomeric glycolic acid equivalents. The selectivity of conversion of formaldehyde is reported as free glycolic acid equivalents. Methanol was present as both free methanol and methyl glycolate, and was converted to free methanol and glycolic acid by the analytical method.

TABLE 22

Feed 1: Rate and Composition

| Ex | g/min | Paraformaldehyde | water | G1 | $H_2SO_4$ |
|---|---|---|---|---|---|
| 154 | 0.68 | 13.8 | 8.3 | 70.2 | 7.7 |
| 155 | 1.01 | 13.8 | 11.7 | 70.0 | 4.5 |
| 156 | 1.01 | 13.8 | 11.6 | 70.0 | 4.5 |
| 157 | 1.66 | 13.0 | 17.2 | 66.0 | 3.8 |
| 158 | 1.02 | 14.4 | 4.3 | 73.2 | 8.0 |
| 159 | 0.94 | 29.8 | 28.6 | 37.8 | 3.8 |

TABLE 23

Overall Feed Ratios and Reaction Conditions

| Ex | Feed Molar Ratio Paraformaldehyde | water | G1 | $H_2SO_4$ | Temp Celsius | Press psig | Res Time minutes |
|---|---|---|---|---|---|---|---|
| 154 | 1.0 | 1.0 | 2.0 | 0.170 | 170 | 1502 | 180 |
| 155 | 1.0 | 1.4 | 2.0 | 0.100 | 200 | 699 | 120 |
| 156 | 1.0 | 1.4 | 2.0 | 0.100 | 190 | 703 | 120 |
| 157 | 1.0 | 2.2 | 2.0 | 0.089 | 205 | 2603 | 72 |
| 158 | 1.0 | 0.5 | 2.0 | 0.170 | 190 | 1901 | 120 |
| 159 | 1.0 | 1.6 | 0.5 | 0.039 | 205 | 2605 | 120 |

TABLE 24

Selectivity, Conversion, and Space-Time Yield Results

| Ex | % F0 Conv | Molar Selectivity G1 | A1 | DG | MGH | MeOH | Space-Time Yield gmol/l-hr |
|---|---|---|---|---|---|---|---|
| 154 | 92 | 94.06 | 1.06 | 3.82 | 0.00 | 1.06 | 1.73 |
| 155 | 87 | 64.56 | 10.72 | 5.56 | 16.86 | 2.29 | 1.05 |
| 156 | 85 | 70.00 | 10.80 | 3.00 | 10.40 | 5.70 | 1.55 |
| 157 | 93 | 89.22 | 2.90 | 4.12 | 1.72 | 2.04 | 3.55 |
| 158 | 97 | 84.63 | 1.24 | 11.97 | 1.85 | 0.32 | 2.51 |
| 159 | 95 | 89.96 | 3.04 | 2.91 | 2.11 | 1.98 | 4.94 |

We claim:

1. A process for the preparation of glycolic acid, comprising
   (A) feeding carbon monoxide, methylene dipropionate, propionic acid, and water to a hydrocarboxylation reaction zone comprising a solid acid catalyst to produce an effluent comprising esters of glycolic and propionic acids;
   (B) hydrolyzing said effluent to produce a hydrolyzed mixture comprising glycolic acid and said propionic acid;

(C) recovering said propionic acid from said hydrolyzed mixture by extracting said hydrolyzed mixture with a hydrophobic solvent selected from at least one of the group consisting of esters having from 4 to 20 carbon atoms, ethers having from 4 to 20 carbon atoms, ketones having from 4 to 20 carbon atoms, and hydrocarbons having from 6 to 20 carbon atoms to form an aqueous raffinate phase comprising a major amount of said glycolic acid contained in said hydrolyzed mixture and an organic extract phase comprising a major amount of said propionic acid contained in said hydrolyzed mixture; and (D) separating said aqueous raffinate phase and said organic extract phase.

2. The process according to claim 1, wherein said feeding of said methylene dipropionate, propionic acid, and water in step (A) occurs at a molar ratio of propionic acid:methylene dipropionate of from 0.01:1 to 6:1 and at a molar ratio of water:methylene dipropionate of from 0.25:1 to 2:1.

3. The process according to claim 1, wherein said feeding of said methylene dipropionate, propionic acid, and water in step (A) occurs at a molar ratio of propionic acid:methylene dipropionate of from 0.01:1 to 3:1 and at a molar ratio of water:methylene dipropionate of from 0.5:1 to 1.5:1.

4. The process according to claim 1, wherein said hydrolyzed mixture comprises said propionic acid, said glycolic acid, and said water in a molar ratio of water:glycolic acid of from 1:1 to 15:1.

5. The process according to claim 1, wherein said hydrolyzed mixture comprises said propionic acid, said glycolic acid, and water in a molar ratio of water:glycolic acid of from 1:1 to 4:1.

6. The process according to claim 1, wherein said hydrophobic solvent is selected from at least one of the group consisting of ethyl acetate, n-propyl acetate, i-propyl acetate, n-butyl acetate, i-butyl acetate, s-butyl acetate, methyl benzoate, i-butyl isobutyrate, 2-ethylhexyl acetate, cyclohexyl acetate, methyl propionate, ethyl propionate, n-propyl propionate, i-propyl propionate, i-butyl propionate, n-butyl propionate, s-butyl propionate, diethyl ether, dipropyl ether, diisopropyl ether, dibutyl ethers, methyl tertiary-butyl ether, methyl tertiary-amyl ether, methyl ethyl ketone, methyl i-butyl ketone, methyl i-propyl ketone, methyl propyl ketone, dibutyl ketone, diisobutyl ketone, isophorone, 3,3,5-trimethylcyclohexanone, cyclohexanone, 2-heptanone, methyl-iso-amyl ketone, diethyl ketone, 5-ethyl 2-nonanone, diamyl ketone, diisoamyl ketone, hexane, heptane, and toluene.

7. The process according to claim 1, wherein greater than 90 weight percent of said propionic acid is recovered in said organic extract phase and wherein greater than 90 weight percent of said glycolic acid is recovered in said aqueous raffinate phase.

8. The process according to claim 1, wherein said extracting in step (C) occurs in a continuous counter-current extractor, wherein said raffinate phase exits the bottom of said extractor and said extract phase exits the top of said extractor, wherein said hydrophobic solvent is fed to said extractor below said hydrolyzed mixture, and wherein the feed ratio of said hydrophobic solvent to said hydrolyzed mixture ranges from 0.5:1 to 20:1 on a weight basis.

9. The process according to claim 8, further comprising feeding a hydrophilic solvent to said extractor above said hydrolyzed mixture, wherein the feed ratio of said hydrophilic solvent to said hydrolyzed mixture ranges from 0.01:1 to 5:1 on a weight basis.

10. The process according to claim 1, wherein the molar ratio of carbon monoxide to methylene dipropionate ranges from 1:1 to 10:1 and said hydrocarboxylation reaction zone is operated at a pressure of from 35 bar gauge to 200 bar gauge and a temperature of from 80° C. to 220° C.

11. The process according to claim 1, wherein said solid acid catalyst is selected from at least one of the group consisting of sulfonic acid resins, silica-aluminate, silica-alumino-phosphates, heteropolyacids, supported heteropolyacids, sulfuric acid treated metal oxides, and phosphoric acid treated metal oxides.

12. The process according to claim 1, further comprising
(E) separating said organic extract phase into said hydrophobic solvent and said propionic acid, recycling said hydrophobic solvent to step (C), and recycling said propionic acid to step (A)
(F) reacting a first ethylene glycol with said aqueous raffinate phase while simultaneously removing water to produce an esterification effluent comprising glycolate ester oligomers and glycolic acid oligomers and an overhead stream comprising water; and
(G) reacting hydrogen with said esterification effluent to produce a second ethylene glycol, separating said second ethylene glycol into a product ethylene glycol and said first ethylene glycol, and recycling said first ethylene glycol to step (F).

13. A process for the preparation of glycolic acid, comprising
(A) feeding carbon monoxide, methylene dipropionate, propionic acid, and water to a hydrocarboxylation reactor zone comprising a solid acid catalyst to produce an effluent comprising esters of glycolic and propionic acids;
(B) hydrolyzing said effluent to produce a hydrolyzed mixture comprising glycolic acid and said propionic acid;
(C) recovering said propionic acid from said hydrolyzed mixture by extracting said hydrolyzed mixture with a hydrophobic solvent selected from at least one of the group consisting of n-propyl acetate, i-propyl acetate, n-butyl acetate, i-butyl acetate, s-butyl acetate, methyl propionate, ethyl propionate, i-propyl propionate, methyl tertiary-butyl ether, methyl i-butyl ketone, methyl i-propyl ketone, methyl propyl ketone, and toluene to form an aqueous raffinate phase comprising a major amount of said glycolic acid contained in said hydrolyzed mixture and an organic extract phase comprising a major amount of said propionic acid contained in said hydrolyzed mixture; and
(D) separating said aqueous raffinate phase and said organic extract phase.

14. The process according to claim 13, wherein feeding of said methylene dipropionate, propionic acid, and water in step (A) occurs at a molar ratio of propionic acid:methylene dipropionate of from 0.01:1 to 3:1 and at a molar ratio of water:methylene dipropionate of from 0.5:1 to 1.5:1.

15. The process according to claim 13, wherein hydrolyzed mixture comprises said propionic acid, said glycolic acid, and said water in a molar ratio of water:glycolic acid of from 1:1 to 4:1.

16. The process according to claim 13, wherein said hydrophobic solvent is selected from at least one of the group consisting of n-propyl acetate, i-propyl acetate, methyl propionate, ethyl propionate, i-propyl propionate, methyl tertiary-butyl ether, and methyl i-butyl ketone.

17. The process according to claim 13, wherein greater than 90 weight percent of said propionic acid is recovered in said organic extract phase and wherein greater than 90 weight percent of said glycolic acid is recovered in said aqueous raffinate phase.

18. The process according to claim 13, wherein said extracting in step (C) occurs in a continuous counter-current extractor, wherein said raffinate phase exits the bottom of said extractor and said extract phase exits the top of said extractor, wherein said hydrophobic solvent is fed to said extractor below said hydrolyzed mixture, and wherein the feed ratio of said hydrophobic solvent to said hydrolyzed mixture ranges from 0.5:1 to 10:1 on a weight basis.

19. The process according to claim 18, further comprising feeding a hydrophilic solvent to said extractor above said hydrolyzed mixture, wherein the feed ratio of said hydrophilic solvent to said hydrolyzed mixture ranges from 0.01:1 to 5:1 on a weight basis, and wherein said feed ratio of said hydrophobic solvent to said hydrolyzed mixture ranges from 0.5:1 to 4:1 on a weight basis.

20. The process according to claim 13, further comprising
(E) separating said organic extract phase into said hydrophobic solvent and said propionic acid, recycling said hydrophobic solvent to step (C), and recycling said propionic acid to step (A);
(F) reacting a first ethylene glycol with said aqueous raffinate phase while simultaneously removing water to produce an esterification effluent comprising glycolate ester oligomers and glycolic acid oligomers and an overhead stream comprising water; and
(G) reacting hydrogen with said esterification effluent to produce a second ethylene glycol, separating said second ethylene glycol into a product ethylene glycol and said first ethylene glycol, recycling said first ethylene glycol to step (F).

* * * * *